(12) United States Patent
Bosmans et al.

(10) Patent No.: US 7,790,750 B2
(45) Date of Patent: *Sep. 7, 2010

(54) BICYCLIC BENZAMIDES OF 3- OR 4-SUBSTITUTED 4-(AMINOMETHYL)-PIPERIDINE DERIVATIVES

(75) Inventors: Jean-Paul René Marie André Bosmans, Rijkevorsel (BE); Michel Anna Jozef De Cleyn, Merksplas (BE); Michel Surkyn, Kessel-lo (BE)

(73) Assignee: Janssen Pharmaceutica N.V., Beerse (BE)

( * ) Notice: Subject to any disclaimer, the term of this patent is extended or adjusted under 35 U.S.C. 154(b) by 20 days.

This patent is subject to a terminal disclaimer.

(21) Appl. No.: 11/584,732

(22) Filed: Oct. 20, 2006

(65) Prior Publication Data
US 2007/0037850 A1    Feb. 15, 2007

Related U.S. Application Data

(60) Continuation of application No. 11/357,884, filed on Feb. 17, 2006, now abandoned, which is a continuation of application No. 10/643,506, filed on Aug. 19, 2003, now abandoned, which is a division of application No. 09/791,227, filed on Feb. 22, 2001, now Pat. No. 6,635,643, which is a continuation of application No. 09/349,912, filed on Jul. 8, 1999, now abandoned.

(30) Foreign Application Priority Data

Jul. 11, 1997   (EP)  .................................. 97202180
Feb. 27, 1998   (EP)  .................................. 98200624

(51) Int. Cl.
*A61K 31/445* (2006.01)
*C07D 407/02* (2006.01)

(52) U.S. Cl. ........................ 514/320; 514/248; 514/258; 514/321; 544/237; 544/278; 546/196; 546/197; 546/205; 546/207; 546/214

(58) Field of Classification Search .................. 514/248, 514/258, 320, 321; 544/237, 278; 546/196, 546/197, 205, 207, 214
See application file for complete search history.

(56) References Cited

U.S. PATENT DOCUMENTS

| | | | |
|---|---|---|---|
| 4,711,703 A | 12/1987 | Lawton | |
| 4,722,630 A | 2/1988 | Fang | |
| 4,853,394 A | 8/1989 | King et al. | |
| 4,910,312 A | 3/1990 | Buchhelt | |
| 5,130,013 A | 7/1992 | Van Daele et al. | |
| 5,185,335 A * | 2/1993 | Van Daele et al. | .......... 514/243 |
| 5,262,418 A | 11/1993 | Van Daele et al. | |
| 5,374,637 A * | 12/1994 | Van Daele et al. | .......... 514/320 |
| 5,452,013 A | 9/1995 | Bosmans et al. | |
| 5,948,794 A | 9/1999 | Van Daele et al. | |
| 6,127,379 A | 10/2000 | King et al. | |
| 6,172,062 B1 | 1/2001 | Clark et al. | |
| 6,452,013 B1 * | 9/2002 | Bosmans et al. | ............ 546/229 |
| 6,635,643 B2 * | 10/2003 | Bosmans et al. | ............ 514/248 |

FOREIGN PATENT DOCUMENTS

| | | |
|---|---|---|
| EP | 0332171 | 8/1989 |
| EP | 0389037 | * 9/1990 |
| EP | 0445862 | 9/1991 |
| EP | 0299566 | 9/1994 |
| EP | 0309043 | 11/1994 |
| EP | 0389037 | 9/1995 |

(Continued)

OTHER PUBLICATIONS

SB205800 Dialog file 452, assess No. 00199407 (1993).*

(Continued)

*Primary Examiner*—Celia Chang
(74) *Attorney, Agent, or Firm*—Woodcock Washburn, LLP

(57) ABSTRACT

The present invention of compounds of formula (I)

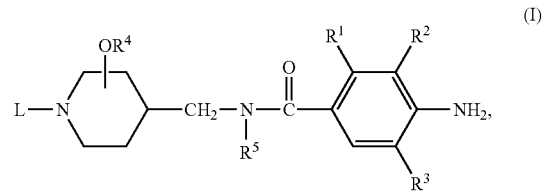

a stereochemically isomeric form thereof, an N-oxide form thereof or a pharmaceutically acceptable acid addition salt thereof, $R^1$ and $R^2$ taken together form a bivalent radical of formula wherein in said bivalent radicals one or two hydrogen atoms may be substituted with $C_{1-6}$alkyl; $R^3$ is hydrogen or halo; $R^4$ is hydrogen or $C_{1-6}$alkyl; $R^5$ is hydrogen or $C_{1-6}$alkyl; L is $C_{3-6}$cycloalkyl, $C_{5-6}$cycloalkanone, $C_{2-6}$alkenyl, or L is a radical of formula -Alk-$R^6$—, Alk-X—$R^7$, -Alk-Y—C(=O)—$R^9$, or -Alk-Y—C(=O)—$NR^{11}R^{12}$ wherein each Alk is $C_{1-12}$alkanediyl; and $R^6$ is hydrogen, cyano, $C_{1-6}$alkylsulfonylamino, $C_{3-6}$cycloalkyl, $C_{5-6}$cycloalkanone, or a heterocyclic ringsystem; $R^7$ is hydrogen, $C_{1-6}$alkyl, hydroxy$C_{1-6}$alkyl, $C_{3-6}$cycloalkyl, or a heterocyclic ringsystem; X is O, S, $SO_2$ or $NR^8$; said $R^8$ being hydrogen or $C_{1-6}$alkyl; $R^9$ is hydrogen, $C_{1-6}$alkyl, $C_{3-6}$cycloalkyl, $C_{1-6}$alkyloxy or hydroxy; Y is $NR^{10}$ or a direct bond; said $R^{10}$ being hydrogen, or $C_{1-6}$alkyl; $R^{11}$ and $R^{12}$ each independently are hydrogen, $C_{1-6}$alkyl, $C_{3-6}$cycloalkyl, or $R^{11}$ and $R^{12}$ combined with the nitrogen atom may form an optionally substituted pyrrolidinyl, piperidinyl, piperazinyl or 4-morpholinyl ring. Processes for preparing said products, formulations comprising said products and their use as a medicine are disclosed, in particular for treating conditions which are related to impairment of gastric emptying.

10 Claims, No Drawings

FOREIGN PATENT DOCUMENTS

| | | |
|---|---|---|
| EP | 0774460 | 5/1997 |
| HU | 196054 | 9/1988 |
| WO | WO 9303725 | 3/1993 |
| WO | WO 9305038 | 3/1993 |
| WO | WO 9316072 | 8/1993 |
| WO | WO 9408995 | 4/1994 |
| WO | WO 9410174 | 5/1994 |
| WO | WO 96/33186 * | 10/1996 |
| WO | WO 9711054 | 3/1997 |
| WO | WO 97/29739 * | 8/1997 |
| WO | WO 9923654 | 5/1999 |

OTHER PUBLICATIONS

Patani et al. "Bioisosterism . . . " Chem. Rev. v.96 p. 3147-3176 (1996).*

Meulemans et al. "Use of 5HT4 receptor . . . " CA 128:226259 (1998).*

Exhibit I.*

Gaster, L. et al., (1-Butyl-4-piperidinyl)methyl 8-amino-7-chloro-1,4-benzodioxane-5-carboxylate Hydrochloride: A Highly Potent and Selective 5-$HT_4$ Receptor Antagonist Derived from Metoclopramide, Journal of Medicinal Chemistry, 1993, vol. 36, No. 25, pp. 4121-4123.

Fancelli, D., et al. Serotoninergic 5-$HT_3$ and 5-$HT_4$ Receptor Activities of Dihydrobenzofuran Carboxylic Acid Derivatives, Bioorganic & Medicinal Chemistry Letters, 1996, vol. 6, No. 3, pp. 263-266.

Lewis, N., et al., Diacetoxypiperidinium Analogs of Acetylcholine, Journal of Medicinal Chemistry, 1973, vol. 16, No. 2, pp. 156-159.

Van Daele et al. "N-3-hydroxy . . . " CA 123:143904 (1995).

Prieto et al. "Piperidinylmethyl . . . " CA 129:316144 (1998).

Itoh et al. "Synthesis and . . . " CA 131:286384 (1999).

* cited by examiner

BICYCLIC BENZAMIDES OF 3- OR 4-SUBSTITUTED 4-(AMINOMETHYL)-PIPERIDINE DERIVATIVES

This is a continuation of U.S. Ser. No. 11/357,884 filed on Feb. 17, 2006, now abandoned which application is a continuation of U.S. Ser. No. 10/643,506, filed on Aug. 19, 2003, now abandoned which is a divisional application of U.S. Ser. No. 09/791,227 filed on Feb. 22, 2001, now U.S. Pat. No. 6,635,643, which is a continuation of U.S. Ser. No. 09/349,912 filed on Jul. 8, 1999 now abandoned which claims priority from U.S. Ser. No. 09/113,635 filed on Jul. 10, 1998, which claims priority to EP application 98.200.624.9 filed Feb. 27, 1998 and EP application 97.202.180.2 filed Jul. 11, 1997.

The present invention is concerned with novel compounds of formula (I) having superior gastrokinetic properties. The invention further relates to methods for preparing such novel compounds, pharmaceutical compositions comprising said novel compounds as well as the use as a medicine of said compounds.

Journal of Medicinal Chemistry, 1993, 36, pp 4121-4123 discloses 4-amino-N-[(1-butyl-4-piperidinyl)methyl]-5-chloro-2-methoxy-benzamide as a potent and selective 5HT$_4$-receptor antagonist.

WO 93/05038, published on Mar. 18, 1993 (SmithKline Beecham PLC) discloses a number of substituted 4-piperidinylmethyl 8-amino-7-chloro-1,4-benzodioxan-5-carboxamides having 5HT$_4$-receptor antagonistic activity.

WO 94/10174, published on May 11, 1994 (SmithKline Beecham PLC) discloses a number of substituted 4-pyridinylmethyl oxazino[3,2-a]indole-carboxamide derivatives having 5HT$_4$-receptor antagonistic activity.

The above prior art documents all disclose substituted 4-piperidinylmethyl carboxamides and the analogues thereof having 5HT$_4$-receptor antagonistic activity. Compounds showing 5HT$_4$ antagonism are taught to have potential interest in the treatment of, for example, irritable bowel syndrome, in particular the diarrhoea aspects of irritable bowel syndrome, i.e. these compounds block the ability of 5HT (which stands for 5-hydroxy-tryptamine, i.e. serotonin) to stimulate gut motility (see WO-93/05038, page 8, lines 12 to 17). The present gastroprokinetic compounds differ in structure mainly by the presence of a hydroxy- or an alkyloxy group on the central piperidine ring.

WO 93/16072, published on Aug. 19, 1993 discloses 5-amino-N-[(1-butyl-4-piperidinyl)methyl]-6-chloro-3,4-dihydro-2H-1-benzopyran-8-carboxamide having 5 HT$_4$ receptor antagonistic activity.

Bioorganic & Medicinal Chem. Lett., 1996, 6, pp. 263-266, and WO-96/33186 (Pharmacia S.P.A.), published on Oct. 24, 1996, disclose 4-amino-N-(1-butyl-4-piperidinyl)methyl-5-chloro-2,3-dihydro-7-benzofurancarboxamide having 5 HT$_4$ receptor agonistic activity.

The compounds of the present invention differ from the previous prior art documents due to the presence of a hydroxy or a $C_{1-6}$alkyloxy group on the 3 position of the central piperidine ring.

EP-0,299,566, published on 18 Jan. 1989, discloses N-(3-hydroxy-4-piperidinyl)benzamides having gastrointestinal motility stimulating activity.

EP-0,309,043, published on 29 Mar. 1989, discloses substituted N-(1-alkyl-3-hydroxy-4-piperidinyl)benzamides having gastrointestinal motility stimulating activity.

EP-0,389,037, published on 26 Sep. 1990, discloses N-(3-hydroxy-4-piperidinyl)(dihydrobenzofuran, dihydro-2H-benzopyran or dihydrobenzodioxin)-carboxamide derivatives having gastrointestinal motility stimulating activity.

The latter three prior art documents all disclose carboxamide derivatives wherein the amide function is bonded directly with the piperidine ring, while the compounds of the present invention all have an amide function wherein a methylene group is present between the carbamoyl nitrogen and the piperidine ring.

EP-0,774,460, published on 21 May 1997, and WO-97/11054, published on 27 Mar. 1997 disclose a number of benzoic acid compounds as 5-HT$_4$ agonists useful for treating gastric motility disorders.

The compounds of the present invention differ from the latter two prior art documents due to the presence of a hydroxy or a $C_{1-6}$alkyloxy group on the 3- or 4-position of the central piperidine ring. Furthermore, those compounds of the present invention wherein $R^2$ is other than hydrogen are also structurally different over said prior art documents.

The problem this invention sets out to solve is to provide compounds having gastrointestinal motility stimulating properties, particularly having superior gastric emptying activity. Preferably said compounds should be orally active.

The solution to this problem is provided by the novel compounds of formula (I) that differ structurally from the prior art, inter alia, by the presence of a hydroxy or a $C_{1-6}$alkyloxy group on the 3- or 4-position of the central piperidine ring, or by the presence of a methylene group between the carbamoyl group and the piperidine ring.

The present invention concerns a compound of formula (I)

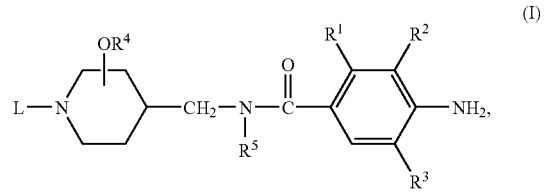

a stereochemically isomeric form thereof, an N-oxide form thereof or a pharmaceutically acceptable acid or base addition salt thereof, wherein $R^1$ and $R^2$ taken together form a bivalent radical of formula

| —O—CH$_2$—O— | (a-1), |
|---|---|
| —O—CH$_2$—CH$_2$— | (a-2), |
| —O—CH$_2$—CH$_2$—O— | (a-3), |
| —O—CH$_2$—CH$_2$—CH$_2$— | (a-4), |
| —O—CH$_2$—CH$_2$—CH$_2$—O— | (a-5), |
| —O—CH$_2$—CH$_2$—CH$_2$—CH$_2$— | (a-6), | wherein in said bivalent radicals one or two hydrogen atoms may be substituted with $C_{1-6}$alkyl, $R^3$ is hydrogen or halo;

$R^4$ is hydrogen or $C_{1-6}$alkyl;

$R^5$ is hydrogen or $C_{1-6}$alkyl;

L is $C_{3-6}$cycloalkyl, $C_{5-6}$cycloalkanone, or $C_{2-6}$alkenyl, or L is a radical of formula -Alk-$R^6$ (b-1), -Alk-X—$R^7$ (b-2), -Alk-Y—C(=O)—$R^9$ (b-3), or -Alk-Y—C(=O)—$NR^{11}R^{12}$ (b-4), wherein each Alk is $C_{1-12}$alkanediyl; and $R^6$ is hydrogen, hydroxy, cyano, $C_{1-6}$alkylsulfonylamino, $C_{3-6}$cycloalkyl, $C_{5-6}$cycloalkanone, or $Het^1$;

$R^7$ is hydrogen, $C_{1-6}$alkyl, hydroxy$C_{1-6}$alkyl, $C_{3-6}$cycloalkyl, or $Het^2$;

X is O, S, $SO_2$ or $NR^8$; said $R^8$ being hydrogen or $C_{1-6}$alkyl;

$R^9$ is hydrogen, $C_{1-6}$alkyl, $C_{3-6}$cycloalkyl, $C_{1-6}$alkyloxy or hydroxy;

Y is $NR^{10}$ or a direct bond; said $R^{10}$ being hydrogen or $C_{1-6}$alkyl;

$R^{11}$ and $R^{12}$ each independently are hydrogen, $C_{1-6}$alkyl, $C_{3-6}$cycloalkyl, or $R^{11}$ and $R^{12}$ combined with the nitrogen atom bearing $R^{11}$ and $R^{12}$ may form a pyrrolidinyl or piperidinyl ring both being optionally substituted with $C_{1-6}$alkyl, amino or mono or di($C_{1-6}$alkyl)amino, or said $R^{11}$ and $R^{12}$ combined with the nitrogen bearing $R^{11}$ and $R^{12}$ may form a piperazinyl or 4-morpholinyl radical both being optionally substituted with $C_{1-6}$alkyl; and $Het^1$ and $Het^2$ each independently are selected from furan; furan substituted with $C_{1-6}$alkyl or halo; tetrahydrofuran; a tetrahydrofuran substituted with $C_{1-6}$alkyl; a dioxolane; a dioxolane substituted with $C_{1-6}$alkyl, a dioxane; a dioxane substituted with $C_{1-6}$alkyl; tetrahydropyran; a tetrahydropyran substituted with $C_{1-6}$alkyl; pyrrolidinyl; pyrrolidinyl substituted with one or two substituents each independently selected from halo, hydroxy, cyano, or $C_{1-6}$alkyl; pyridinyl; pyridinyl substituted with one or two substituents each independently selected from halo, hydroxy, cyano, $C_{1-6}$alkyl; pyrimidinyl; pyrimidinyl substituted with one or two substituents each independently selected from halo, hydroxy, cyano, $C_{1-6}$alkyl, $C_{1-6}$alkyloxy, amino and mono and di($C_{1-6}$alkyl)amino; pyridazinyl; pyridazinyl substituted with one or two substituents each independently selected from hydroxy, $C_{1-6}$alkyloxy, $C_{1-6}$alkyl or halo; pyrazinyl; pyrazinyl substituted with one ore two substituents each independently selected from halo, hydroxy, cyano, $C_{1-6}$alkyl, $C_{1-6}$alkyloxy, amino, mono- and di($C_{1-6}$alkyl)amino and $C_{1-6}$alkyloxycarbonyl;

$Het^1$ can also be a radical of formula

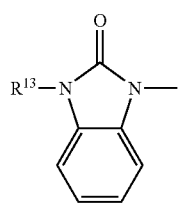
(c-1)

-continued

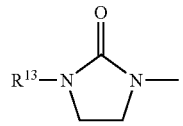
(c-2)

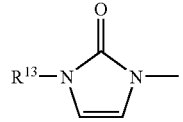
(c-3)

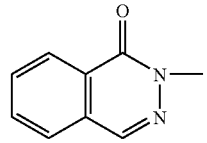
(c-4)

$Het^1$ and $Het^2$ each independently can also be selected from the radicals of formula

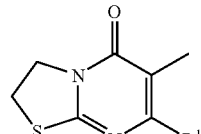
(d-1)

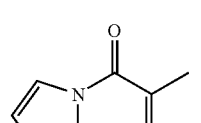
(d-2)

(d-3)

$R^{13}$ and $R^{14}$ each independently are hydrogen or $C_{1-4}$alkyl.

As used in the foregoing definitions halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like; $C_{1-6}$alkyl is meant to include $C_{1-4}$alkyl and the higher homologues thereof having 5 or 6 carbon atoms, such as, for example, 2-methyl-butyl, pentyl, hexyl and the like; $C_{3-6}$cycloalkyl is generic to cyclopropyl, cyclobutyl, cyclopentyl and cyclohexyl; $C_{2-6}$alkenyl defines straight and branched chain unsaturated hydrocarbon radicals having from 2 to 6 carbon atoms, such as ethenyl, propenyl, butenyl, pentenyl or hexenyl; $C_{1-12}$alkanediyl defines bivalent straight or branched chain hydrocarbon radicals containing from 1 to 12 carbon atoms such as, for example, 1,2-ethanediyl, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl and the branched isomers thereof. $C_{1-6}$alkanediyl is defined in an analogous way as $C_{1-12}$alkanediyl.

The —$OR^4$ radical is preferably situated at the 3- or 4-position of the piperidine moiety.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

Some of the compounds of formula (I) may also exist in their tautomeric form. Such forms although not explicitly indicated in the above formula are intended to be included within the scope of the present invention. For instance, when an aromatic heterocyclic ring is substituted with hydroxy the keto-form may be the mainly populated tautomer.

The N-oxide forms of the compounds of formula (I), which may be prepared in art-known manners, are meant to comprise those compounds of formula (I) wherein one or several nitrogen atoms are oxidized to the N-oxide. Particularly those N-oxides are envisaged wherein the piperidine-nitrogen is N-oxidized.

A group of interesting compounds consists of those compounds of formula (I) wherein one or more of the following restrictions apply:
a) $R^1$ and $R^2$ taken together form a radical of formula (a-1), (a-2), (a-3), (a-4), (a-5) or (a-6), wherein optionally one or two hydrogen atoms are substituted with $C_{1-4}$alkyl;
b) $R^3$ is fluoro, chloro or bromo; in particular chloro;
c) $R^4$ is hydrogen or methyl, and the —$OR^4$ radical is situated at the 3- or 4-position of the piperidine ring; or
d) $R^5$ is hydrogen.

More interesting compounds are those compounds of formula (I) wherein $R^1$ and $R^2$ taken together form a radical of formula (a-2), or (a-4), wherein optionally one or two hydrogen atoms are substituted with methyl.

Further more interesting compounds are those interesting compounds of formula (I) wherein $R^4$ is hydrogen or methyl.

Particular compounds are those more interesting compounds wherein the —$OR^4$ radical is situated at the 3-position of the central piperidine moiety having the trans configuration, i.e. the —$OR^4$ radical is in the trans position in relation to the methylene on the central piperidine moiety.

Other particular compounds are those more interesting compounds wherein the —$OR^4$ radical is situated at the 4-position of the central piperidine moiety.

Very particular compounds are those compounds wherein L is:

$C_{3-6}$cycloalkyl or $C_{2-6}$alkenyl; or a radical of formula (b-1), wherein each Alk is $C_{1-6}$alkanediyl, and $R^6$ is hydrogen, hydroxy, cyano, amino, $C_{1-6}$alkylsulfonylamino, $C_{3-6}$cycloalkyl or $Het^1$; wherein $Het^1$ is tetrahydrofuran; dioxolane; dioxolane substituted with $C_{1-6}$alkyl; tetrahydropyran; pyridazinyl substituted with one or more substituents selected from hydroxy, halo and $C_{1-6}$alkyl; or a radical of formula (c-1), (c-3) or (c-4) wherein $R^{13}$ is $C_{1-4}$alkyl; or a radical of formula (b-2), wherein Alk is $C_{1-6}$alkanediyl, X is O, and $R^7$ is $C_{1-6}$alkyl or hydroxy$C_{1-6}$alkyl; or a radical of formula (b-2), wherein Alk is $C_{1-6}$alkanediyl, $R^7$ is $Het^2$ wherein $Het^2$ is pyrazinyl substituted with $C_{1-6}$alkyl, and X is $NR^8$ wherein $R^8$ is hydrogen or $C_{1-6}$alkyl; or a radical of formula (b-3) wherein Y is a direct bond, and $R^9$ is $C_{1-6}$alkyl, hydroxy or $C_{1-6}$alkyloxy; or a radical of formula (b-4) wherein Y is a direct bond, and $R^{11}$ and $R^{12}$ are $C_{1-6}$alkyl, or $R^{11}$ and $R^{12}$ combined with the nitrogen atom bearing $R^{11}$ and $R^{12}$ form pyrrolidinyl.

Preferred compounds are those compounds wherein L is butyl; propyl substituted with methoxy, methylcarbonyl or 2-methyl-1,3-dioxolane; ethyl substituted with 4-methyl-2-pyridazinone or tetrahydropyranyl; or methyl substituted with tetrahydrofuranyl or tetrahydropyranyl.

Most preferred are:

trans-4-amino-N-[(1-butyl-3-hydroxy-4-piperidinyl)methyl]-5-chloro-2,3-dihydro-7-benzofurancarboxamide, trans-4-amino-5-chloro-2,3-dihydro-N-[[3-hydroxy-1-(3-methoxypropyl)-4-piperidinyl]methyl]-7-benzofurancarboxamide, trans-4-amino-5-chloro-2,3-dihydro-N-[3-hydroxy-1-[(tetrahydro-2-furanyl)methyl]-4-piperidinyl]-7-benzofurancarboxamide, trans-4-amino-5-chloro-2,3-dihydro-N-[[3-hydroxy-1-(4-oxopentyl)-4-piperidinyl]methyl]-7-benzofurancarboxamide, trans-4-amino-5-chloro-2,3-dihydro-N-[3-hydroxy-1-[(tetrahydro-2-pyranyl)methyl]-4-piperidinyl]-7-benzofurancarboxamide, trans-4-amino-5-chloro-2,3-dihydro-N-[[3-methoxy-1-(3-methoxypropyl)-4-piperidinyl]methyl]-7-benzofurancarboxamide, trans-4-amino-5-chloro-2,3-dihydro-N-[[3-methoxy-1-[(tetrahydro-2-furanyl)methyl]-4-piperidinyl]methyl]-7-benzofurancarboxamide, trans-4-amino-5-chloro-2,3-dihydro-N-[[3-hydroxy-1-(3-methoxypropyl)-4-piperidinyl]methyl]-2,2-dimethyl-7-benzofurancarboxamide, trans-4-amino-5-chloro-2,3-dihydro-N-[[3-methoxy-1-(4-oxopentyl)-4-piperidinyl]methyl]-7-benzofurancarboxamide, trans-5-amino-N-[(1-butyl-3-hydroxy-4-piperidinyl)methyl]-6-chloro-3,4-dihydro-2H-1-benzopyran-8-carboxamide, and the stereoisomeric forms, the pharmaceutically acceptable acid or base addition salts, or the N-oxides thereof; and trans-(−)-4-amino-5-chloro-2,3-dihydro-N-[[3-hydroxy-1-(3-methoxypropyl)-4-piperidinyl]methyl]-2,2-dimethyl-7-benzofurancarboxamide, a pharmaceutically acceptable acid addition salt or an N-oxide form thereof.

The compounds of the present invention can generally be prepared by N-alkylating an intermediate of formula (III) with an intermediate of formula (II), wherein W is an appropriate leaving group such as, for example, halo, e.g. fluoro, chloro, bromo, iodo, or in some instances W may also be a sulfonyloxy group, e.g. methanesulfonyloxy, benzenesulfonyloxy, trifluoromethanesulfonyloxy and the like reactive leaving groups. The reaction can be performed in a reaction-inert solvent such as, for example, acetonitrile, and optionally in the presence of a suitable base such as, for example, sodium carbonate, potassium carbonate or triethylamine. Stirring may enhance the rate of the reaction. The reaction may conveniently be carried out at a temperature ranging between room temperature and the reflux temperature of the reaction mixture.

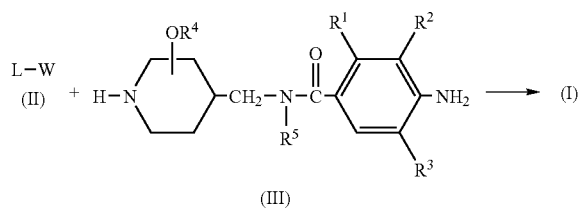

Alternatively, compounds of formula (I) can also be prepared by reductively N-alkylating an intermediate of formula (III) with an intermediate of formula L'=O (IV), wherein L'=O represents a derivative of formula L-H wherein two geminal hydrogen atoms are replaced by oxygen, following art-known reductive N-alkylation procedures.

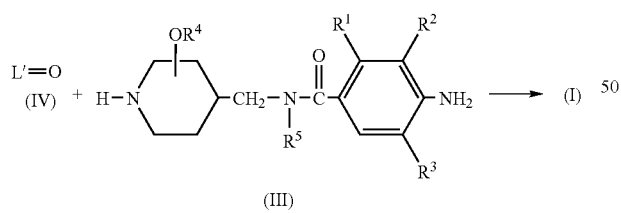

Said reductive N-alkylation can be performed in a reaction-inert solvent such as, for example; dichloromethane, ethanol, toluene or a mixture thereof, and in the presence of a reducing agent such as, for example, a borohydride, e.g. sodium borohydride, sodium cyanoborohydride or triacetoxy borohydride. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. To enhance the rate of the reaction, the temperature may be elevated in a range between room temperature and the reflux temperature of the reaction mixture and optionally the pressure of the hydrogen gas may be raised.

The compounds of formula (I) may be prepared by reacting an intermediate of formula (V) with an carboxylic acid derivative of formula (VI) or a reactive functional derivative thereof, such as for example carbonyl imidazole derivatives. Said amide-bond formation may be performed by stirring the reactants in an appropriate solvent, optionally in the presence of a base, such as sodium imidazolide.

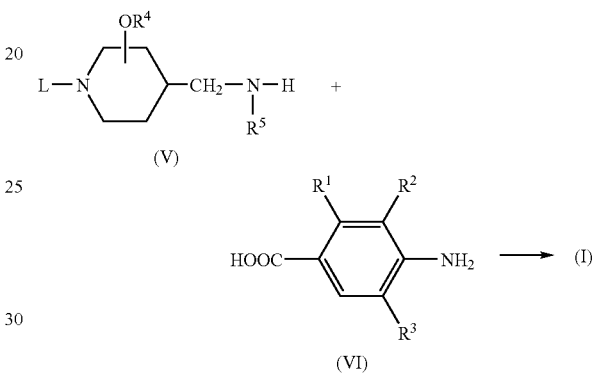

Further, compounds of formula (I) can be prepared by carbonylation of an intermediate of formula (VII), wherein X is bromo or iodo, in the presence of an intermediate of formula (V).

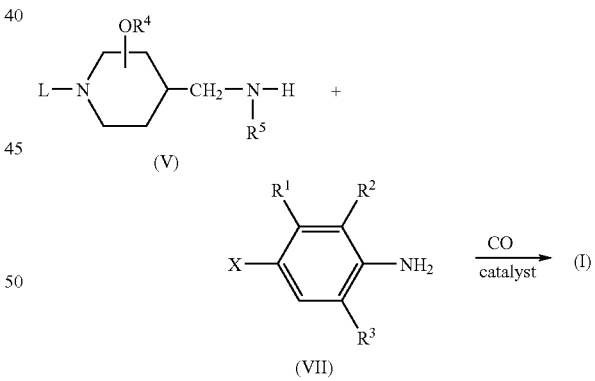

Said carbonylation reaction can be carried out in a reaction-inert solvent such as, e.g. acetonitrile or tetrahydrofuran, in the presence of a suitable catalyst and a suitable base such as a tertiary amine e.g. triethylamine, and at a temperature ranging between room temperature and the reflux temperature of the reaction mixture. Suitable catalysts are, for instance, palladium(triphenylphosphine) complexes. Carbon monoxide is administered at atmospheric pressure or at an increased pressure. Analogous carbonylation reactions are described in Chapter 8 of "Palladium reagents in organic syntheses", Academic Press Ltd., Benchtop Edition 1990, by Richard F. Heck; and the references cited therein.

Said amide formation reaction is known from the above mentioned reference with metal catalysts which are soluble such as palladium(triphenylphosphine) complexes. Unexpectedly, we deem to have found that these reactions can also be performed on metal catalysts which are insoluble or immobilized on a solid carrier. Suitable catalysts are for example palladium-on-carbon, Raney nickel or $Cu_2O$. These insoluble catalysts or catalysts on a solid phase are much less expensive than the metal complexes and are often much easier to handle when synthesis is done on an industrial scale.

In other words, we have found a novel and inventive way to prepare amides in the following way:

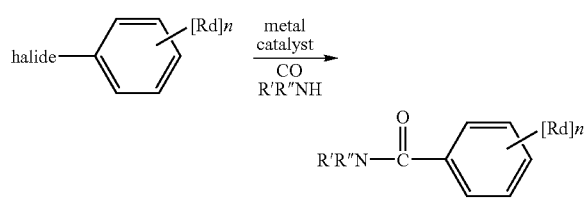

In the above formulas Rd represent any substituent possible on a phenyl, n is an integer from 1 to 5, and R'R" NH can be any primary or secundary amine. The term halide suitably refers to chloro, bromo, iodo. Preferred halides are bromo and iodo.

The preferred catalyst is palladium-on-carbon.

The pressure of CO, i.e. carbon monoxide, may vary according to the substrates and reactants and a person skilled in the art will certainly be able to find a suitable range after little straightforward experimentation. The preferred pressure of CO, i.e. carbon monoxide, is 50 kg/cm² (about 4.9×10⁶ Pa). It may suitably range between about 1 kg/cm² (about 1×10⁵ Pa) and about 100 kg/cm² (about 10×10⁶ Pa).

The reaction temperature may range from room temperature to the reflux temperature of the reaction mixture.

This reaction is preferably performed in a solvent, which can be in the amine R'R" NH itself, or in acetonitrile or in tetrahydrofuran.

Preferably said R'R" NH amine is a primary amine.

Suitably a base is also present. An interesting suitable base is for instance triethylamine.

The starting materials and some of the intermediates are known compounds and are commercially available or may be prepared according to conventional reaction procedures generally known in the art. For example, a number of intermediates of formula (VI) may be prepared according to art-known methodologies described in EP-0,389,037.

However, some intermediates of formula (VI) are novel and, hence, the invention also provides novel intermediates of formula (VI) wherein $R^1$ is methoxy, $R^2$ is methyl or methoxy and $R^3$ is chloro. Said novel intermediates of formula (VI) are prepared as described in Example A.3.

An intermediate of formula (III) may be prepared by reacting an intermediate of formula (VIII), wherein PG represents an appropriate protective group, such as for example a tert-butoxycarbonyl or a benzyl group or a photoremovable group, with an acid of formula (VI), or an appropriate reactive functional derivative thereof, such as for example carbonyl imidazole derivatives, and subsequent deprotection of the thus formed intermediate, i.e. removal of PG by art-known methods.

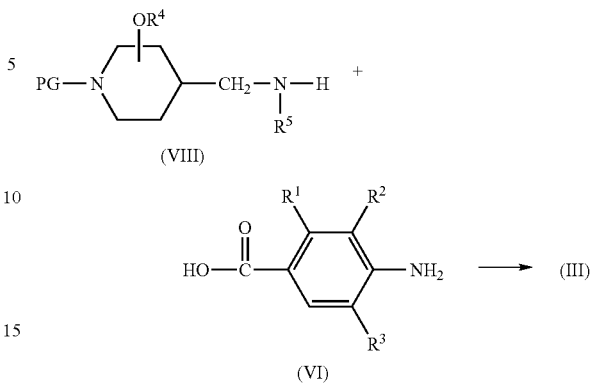

An intermediate of formula (V) may be prepared by reacting an intermediate of formula (X), with an intermediate of formula (II). Said intermediate of formula (X) may be prepared by deprotection of an intermediate of formula (VIII).

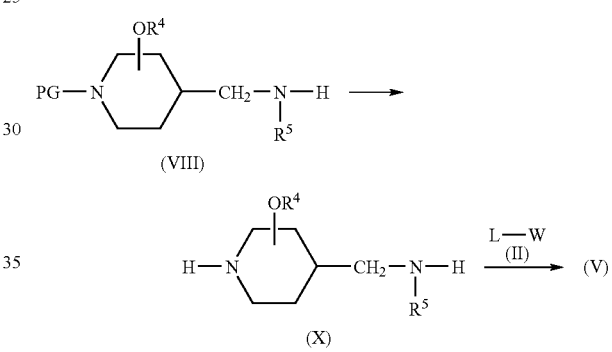

In some cases, it may be appropriate to protect the amine functionality bearing the $R^5$ radical in the above described reaction sequence. Protecting groups for amine functionalities are art-known. These protecting groups may then be removed at the appropriate time during the further synthesis.

Intermediates of formula (VIII-a), being intermediates of formula (VIII) wherein $PG^1$ is a protecting group which cannot be removed by hydrogenation such as e.g. a tert-butoxycarbonyl, can be prepared according to scheme 1.

Scheme 1

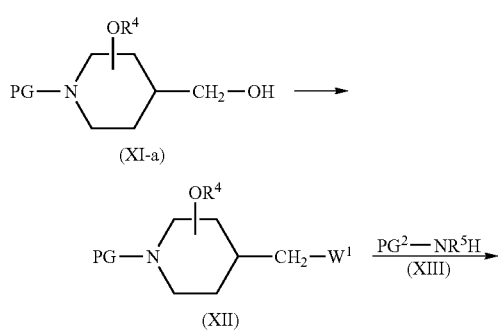

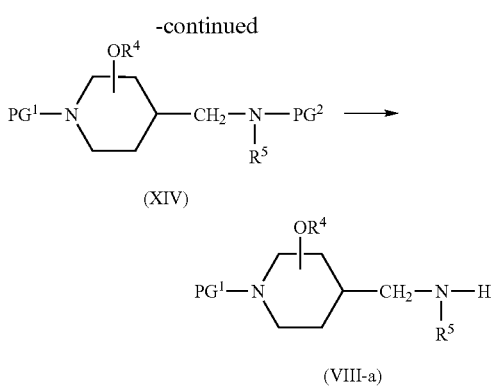

In scheme 1, an intermediate of formula (XI-a) is converted to an intermediate of formula (XII), wherein $W^1$ is a leaving group such as halo or sulfonyloxy. Subsequently, intermediate (XII) is treated with an intermediate of formula (XIII), wherein $PG^2$ is a protecting group which can be removed by hydrogenation such as, e.g. benzyl. Removal of the protecting group $PG^2$ from intermediate (XIV) yields intermediates of formula (VIII-a).

Intermediates of formula (VIII-a-1), defined as intermediates of formula (VIII-a) wherein $R^4$ is methyl, can be prepared as described in scheme 2.

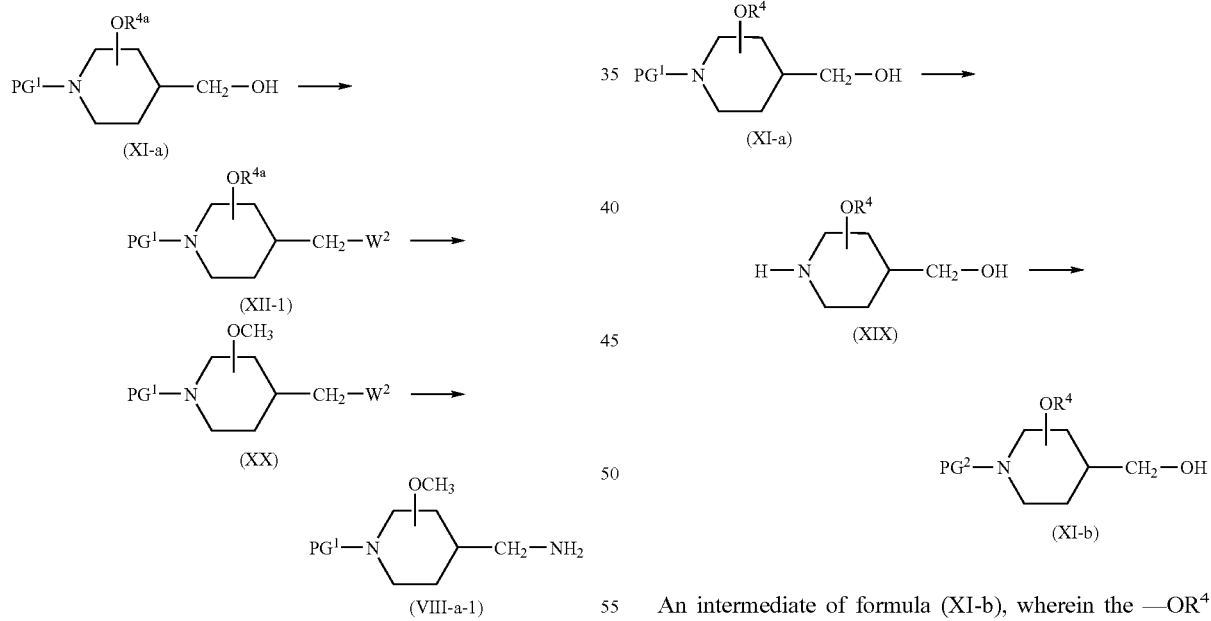

In scheme 2, an intermediate of formula (XI-a), wherein $R^{4a}$ is hydrogen, is converted to an intermediate of formula (XII-1), wherein $W^2$ is a suitable leaving group such as e.g. a tosylate group. Subsequently, the secundary hydroxy of intermediate (XII-1), i.e. the —$OR^{4a}$ moiety, is converted to a methoxy using suitable methylation conditions such as e.g. treatment with sodium hydride in tetrahydrofuran and addition of methyliodide. Conversion of intermediate (XX) to intermediate (VIII-a-1) can be done using art-known reaction procedures.

In an aspect of the present invention, novel compounds of formula (IX) are provided wherein $R^{15}$ and $R^{16}$ are each independently selected from hydrogen or a protective group PG, and $R^4$ and $R^5$ are as defined above. Suitable protecting groups PG are, e.g. $C_{1-4}$alkylcarbonyl, $C_{1-4}$alkyloxycarbonyl, trihalomethylcarbonyl, diphenylmethyl, triphenylmethyl or arylmethyl, wherein aryl is phenyl optionally substituted with up to two substituents selected from $C_{1-4}$alkyloxy or halo. Said novel compounds of formula (IX) comprise the intermediates of formula (VIII), (X) and (XIV).

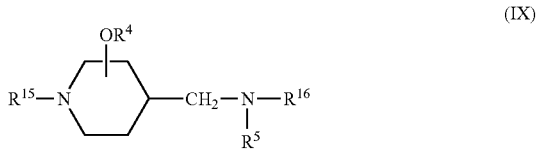

Intermediates of formula (XI-a), wherein $PG^1$ is a protecting group which cannot be removed by hydrogenation such as e.g. a tert-butoxycarbonyl, can be converted to intermediates of formula (XI-b), wherein $PG^2$ is a protecting group which can be removed by hydrogenation such as, e.g. benzyl, using an appropriate deprotection-protection reaction sequence. Conversely, intermediates of formula (XI-b) can also be converted to intermediates of formula (XI-a).

An intermediate of formula (XI-b), wherein the —$OR^4$ moiety is located on the 3-position of the piperidine moiety, $R^4$ is a hydrogen and $PG^2$ is a benzyl group, having the trans configuration, is known from *J. Med. Chem.*, 16, pp. 156-159 (1973). Said article also describes an intermediate of formula (XIX), wherein the —$OR^4$ moiety is located on the 3-position of the piperidine moiety and $R^4$ is a hydrogen, having the trans configuration.

Intermediates of formula (XI-1-a) are defined as intermediates of formula (XI-a) wherein the —$OR^4$ moiety is located on the 3-position of the piperidine moiety.

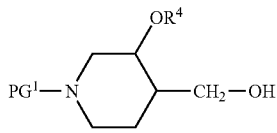

Those intermediates of formula (XI-1-a) wherein $R^4$ is $C_{1-6}$alkyl and having the cis configuration can be prepared by hydrogenating an intermediate of formula (XVI) following art-known methods. The intermediate (XVI), wherein $PG^1$ and $PG^2$ are as defined above, can be prepared by reacting a protected piperidone of formula (XV) with a phosphonium reagent of formula $[(aryl)_3P—CH_2—O—PG^2]^+$-halide$^-$, in appropriate conditions for carrying out a Wittig-type reaction. Subsequent removal of $PG^2$ yields intermediates of formula (XI-1-a) having the cis configuration.

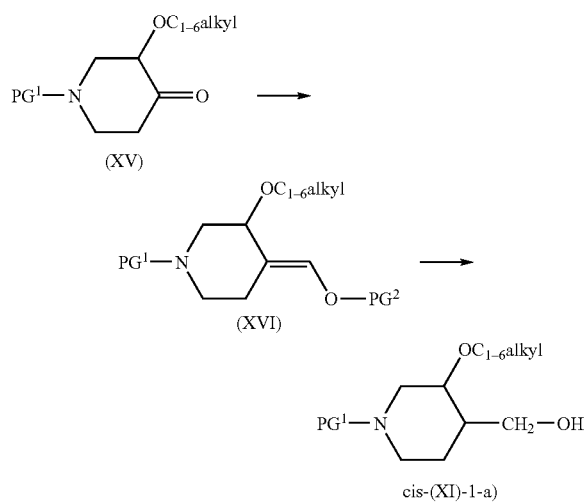

A novel way of preparing an intermediate of formula (XI-1-b) having the trans-configuration was found. Said novel preparation starts from an intermediate of formula (XI-1-b) having the cis-configuration or from an intermediate of formula (XVII) having the cis-configuration. In said intermediates of formula (XI-1-b) and (XVII) $PG^2$ is as defined above, $R^{4a}$ is hydrogen, $C_{1-6}$alkyl or a protective group such as for example, benzyl, tert-butoxycarbonyl and the like.

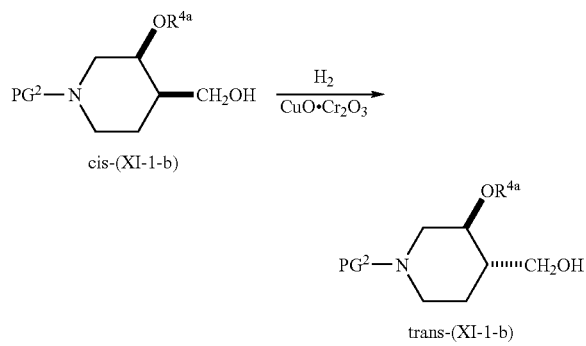

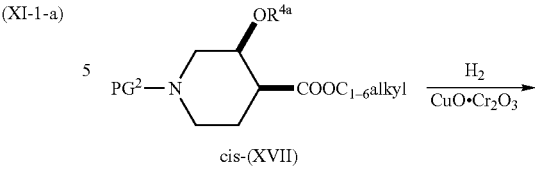

Said inversion-reaction is carried out in an appropriate solvent, such as, for example an ether, e.g. tetrahydrofuran in the presence of $CuO.Cr_2O_3$ under a hydrogen atmosphere and in the presence of an appropriate base, such as, for example calciumoxide.

The preferred hydrogen pressure and reaction temperature is dependent upon the starting material. Starting from cis-(XI-1-b) the hydrogen pressure preferably ranges from 900 to 2000 kPa (measured at room temperature) and the reaction temperature ranges from room temperature up to 200° C., preferably the reaction temperature is about 120° C.

When starting from cis-(XVII), the preferred hydrogen pressure range is from 1500 kPa to 2200 kPa, preferably between 1800 kPa to 2000 kPa. The reaction temperature is between 100° C. and 200° C. preferably at about 125° C. Apparently an equilibrium is reached, typically with a diastereomeric ratio of about 65:35 (trans:cis) as determined by gas chromatography. However via recrystallization it is possible to purify the desired trans-isomer. A suitable solvent for recrystallization is an ether, e.g. diisopropyl ether.

The pure intermediate of formula trans-(XI-1-b) having the trans configuration can also be obtained by chromatographic techniques, such as, for example gravitation chromatography or (H)PLC, starting from the cis/trans mixture of the intermediate (XI-1-b).

Still another novel way of preparing intermediates of formula trans-(XI-1-b) is to react an intermediate of formula (XVIII) with borane or a borane derivative. Borane itself is commercially available as a borane-tetrahydrofuran complex. Borane derivatives, especially chiral borane derivatives are also commercially available. The reaction with borane is performed in a reaction inert solvent, preferable an ether, e.g. tetrahydrofuran. While adding the borane or the borane derivative the reaction mixture is kept at temperatures below 0° C., interestingly at a temperature of about −30° C. After adding the borane or the borane derivative to the reaction mixture the mixture is allowed to heat up while stirring is continued. The mixture is stirred for several hours. Subsequently, a hydroxide, e.g. sodium hydroxide is added as well as a peroxide, e.g. hydrogen peroxide and the reaction mixture is stirred at elevated temperatures for several hours. After this treatment the reaction product was isolated in art-known manner.

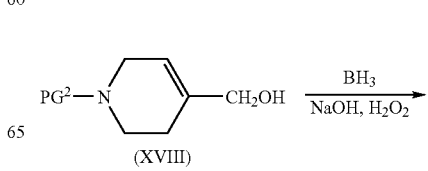

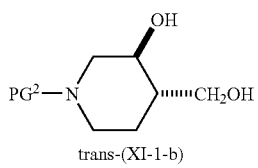

trans-(XI-1-b)

Intermediates of formula (XVIII) can be prepared by reacting an intermediate of formula (XXI), wherein PG² is as defined above and W is a leaving group as defined above, with an intermediate of formula (XXII), and subsequent reduction of the so-obtained intermediate (XXIII) with sodium borohydride, yielding intermediates of formula (XVIII).

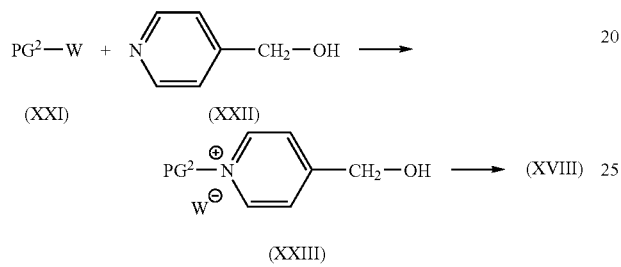

Said reaction procedure can also be used to prepare intermediates of formula (V). Consequently, an intermediate of formula (II) is reacted with an intermediate of formula (XXII) and the so-obtained intermediate of formula (XXIV) is reduced to an intermediate of formula (XXV) using sodium borohydride. Subsequently, the intermediates of formula (XXV) are converted to intermediates of formula (XXVI) using the above-described reaction procedure for the conversion of intermediates (XVIII) to intermediates of formula trans-(XI-b).

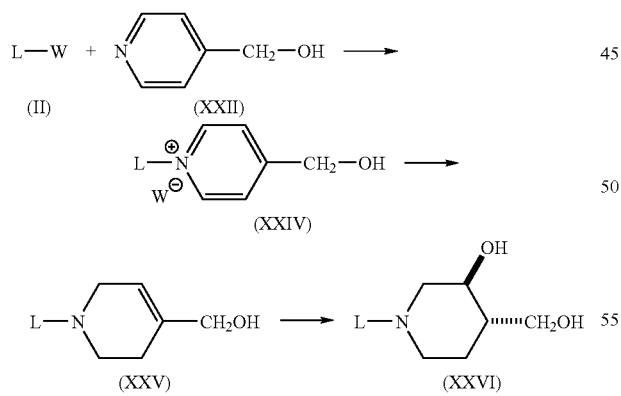

Intermediates of formula (XXVI) can be converted to intermediates of formula (V) having the trans configuration, using a reaction procedure as describe above in Scheme 1 or Scheme 2.

Intermediates of formula (VIII-a) are defined as intermediates of formula (VIII) wherein the —OR⁴ moiety is located on the 4-position of the piperidine moiety and R⁴ is hydrogen.

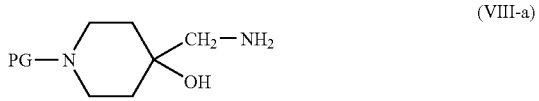

Said intermediates of formula (VIII-a) can be prepared by reacting an intermediate of formula (XXVII) with nitromethane under suitable reaction conditions, such as, e.g. sodium methoxide in methanol, and subsequently converting the nitro group into an amine group, thereby yielding the intermediates of formula (VIII-a).

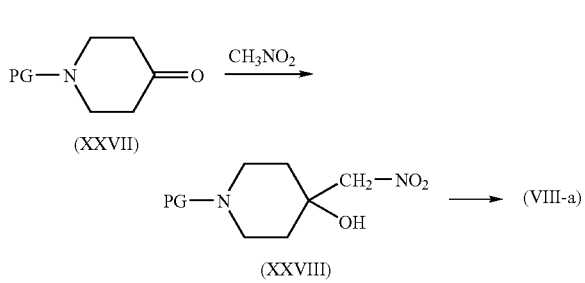

Intermediates of formula (V-a), defined as intermediates of formula (V) wherein R⁵ is hydrogen, can be prepared as following:

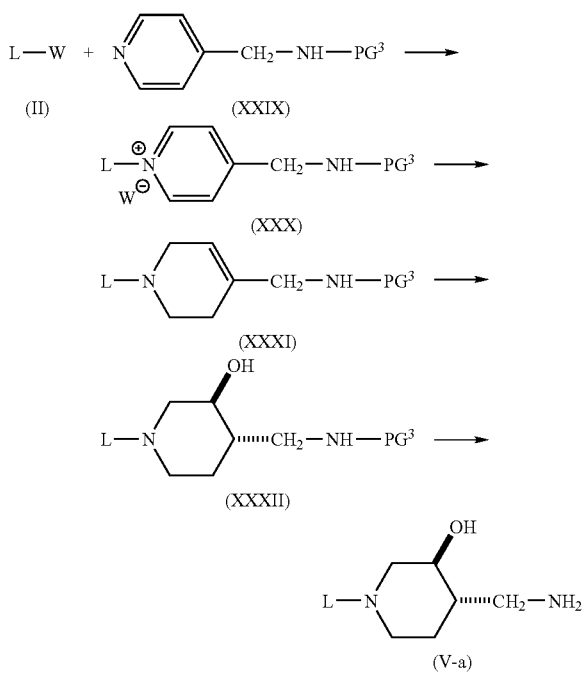

An intermediate of formula (II) is reacted with an intermediate of formula (XXIX), wherein PG³ is a suitable protecting group such as p-toluenesulfonyl, and the so-obtained intermediate of formula (XXX) is reduced to an intermediate of formula (XXXI) using sodium borohydride. Subsequently, the intermediates of formula (XXXI) are converted to intermediates of formula (XXXII) using the above-described reaction procedure for the conversion of intermediates (XVIII) to intermediates of formula trans-(XI-b). Subsequently, removing the protecting group $PG^3$ from intermediates (XXXII) yields the intermediates of formula (V-a).

The compounds of formula (I), the N-oxide forms, the pharmaceutically acceptable salts and stereoisomeric forms thereof possess favourable intestinal motility stimulating properties. In particular the present compounds show significant gastric emptying activity as is evidenced in pharmacological example C-1, the "Gastric emptying of an acaloric liquid meal delayed by administration of lidamidine in conscious dogs"-test.

The compounds of formula (I) also are shown to have a beneficial effect such as increase of basal pressure of the LES, i.e. Lower Esophageal Sphincter.

Most of the intermediates of formula (III) have shown to have analogous activity as the final compounds of formula (I).

In view of the capability of the compounds of the present invention to enhance the gastrointestinal motility, and in particular to activate gastric emptying, the subject compounds are useful to treat conditions related to a hampered or impaired gastric emptying and more generally to treat conditions related to a hampered or impaired gastrointestinal transit.

In view of the utility of the compounds of formula (I), it follows that the present invention also provides a method of treating warm-blooded animals, including humans, (generally called herein patients) suffering from conditions related to a hampered or impaired gastric emptying or more generally suffering from conditions related to a hampered or impaired gastrointestinal transit. Consequently a method of treatment is provided for relieving patients suffering from conditions, such as, for example, gastro-oesophageal reflux, dyspepsia, gastroparesis, constipation, post-operative ileus, and intestinal pseudo-obstruction. Gastroparesis can be brought about by an abnormality in the stomach or as a complication of diseases such as diabetes, progressive systemic sclerosis, anorexia nervosa and myotonic dystrophy. Constipation can result from conditions such as lack of intestinal muscle tone or intestinal spasticity. Post-operative ileus is an obstruction or a kinetic impairment in the intestine due to a disruption in muscle tone following surgery. Intestinal pseudo-obstruction is a condition characterized by constipation, colicky pain, and vomiting, but without evidence of physical obstruction. The compounds of the present invention can thus be used either to take away the actual cause of the condition or to relief the patients from symptoms of the conditions. Dyspepsia is an impairment of the function of digestion, that can arise as a symptom of a primary gastrointestinal dysfunction, especially a gastrointestinal dysfunction related to an increased muscle tone or as a complication due to other disorders such as appendicitis, galbladder disturbances, or malnutrition.

The symptoms of dyspepsia may also arise due to the intake of chemical substances, e.g. Selective Seretonine Reuptake Inhibitors (SSRI's), such as fluoxetine, paroxetine fluvoxamine, and sertraline.

Additionally some of the compounds also are stimulators of kinetic activity on the colon.

Hence, the use of a compound of formula (I) as a medicine is provided, and in particular the use of a compound of formula (I) for the manufacture of a medicine for treating conditions involving a decreased gastro-intestinal motility, in particular decreased gastric emptying. Both prophylactic and therapeutic treatment are envisaged.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxypropyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

The formulations of the present invention may optionally include an anti-flatulent, such as simethicone, alpha-D-galactosidase and the like.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents. Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glycerides.

For intranasal administration the compounds of the invention may be used, for example, as a liquid spray, as a powder or in the form of drops.

In general it is contemplated that a therapeutically effective amount would be from about 0.001 mg/kg to about 2 mg/kg body weight, preferably from about 0.02 mg/kg to about 0.5 mg/kg body weight. A method of treatment may also include administering the active ingredient on a regimen of between two or four intakes per day.

EXPERIMENTAL PART

In the procedures described hereinafter the following abbreviations were used: "ACN" stands for acetonitrile; "THF", which stands for tetrahydrofuran; "DCM" stands for dichloromethane; "DEPE" stands for diisopropylether; "EtOAc" stands for ethyl acetate; "$NH_4OAc$" stands for ammonium acetate; "HOAc" stands for acetic acid; "MIK" stands for methyl isobutyl ketone.

For some chemicals the chemical formula was used, e.g. NaOH for sodium hydroxide, $K_2CO_3$ for potassium carbonate, $H_2$ for hydrogen gas, $MgSO_4$ for magnesium sulfate, $CuO.Cr_2O_3$ for copper chromite, $N_2$ for nitrogen gas, $CH_2Cl_2$ for dichloromethane, $CH_3OH$ for methanol, $NH_3$ for ammonia, HCl for hydrochloric acid, NaH for sodium hydride, $CaCO_3$ for calcium carbonate, CO for carbon monoxide, and KOH for potassium hydroxide.

Of some compounds of formula (I) the absolute stereochemical configuration was not experimentally determined. In those cases the stereochemically isomeric form which was first isolated is designated as "A" and the second as "B", without further reference to the actual stereochemical configuration.

A. Preparation of the Intermediates

Example A.1 a) A solution of 4-pyridinemethanol (1.84 mol) in ACN (1000 ml) was added to a solution of benzylchloride (2.2 mol) in ACN (1000 ml) and the reaction mixture was refluxed for 3 hours, cooled to room temperature and evaporated. The residue was suspended in diethylether, filtered and dried, yielding 1-(phenylmethyl)-4-(hydroxy-methyl)-pyridinyl chloride (411 g, 97%).

b) 1-(Phenylmethyl)-4-(hydroxymethyl)-pyridinyl chloride (0.87 mol) was dissolved in methanol (2200 ml) and cooled to −20° C. Sodium borohydride (1.75 mol) was added portionwise under a nitrogen atmosphere. The reaction mixture was stirred for 30 minutes and water (200 ml) was added dropwise. The reaction mixture was partially evaporated, water was added and the reaction mixture was extracted with DCM. The organic layer was separated, dried, filtered and evaporated. The residue was purified over silica gel (eluent: DCM), yielding 155 g of 1,2,3,6-tetrahydro-1-(phenylmethyl)-4-pyridinemethanol.

Example A.2 a) A solution of 1,2,3,6-tetrahydro-1-(phenylmethyl)-4-pyridinemethanol (0.5 mol) in THF (1000 ml) was cooled to −30° C. and was added dropwise under a nitrogen atmosphere to a solution of borane in THF (1 M, 1000 ml) while the reaction mixture was kept at a temperature between −20° C. and −30° C. After the addition, the reaction mixture was stirred for 4 hours, allowed to warm up to room temperature and stirred at room temperature for 18 hours. The reaction mixture was cooled to −10° C. and water (25 ml) was added dropwise. Then, simultaneously, NaOH (3M in water, 70 ml) and the hydrogen peroxide (30% solution in water, 63.3 ml) was added dropwise while the reaction mixture was kept at a temperature of −10° C.

Again NaOH (50% in water, 140 ml) was added. The reaction mixture was stirred at reflux for 4 hours. The reaction mixture was cooled and filtered. The filtrate was evaporated. The resulting precipitate was dissolved in water (500 ml) and saturated with $K_2CO_3$. The product was extracted with DCM. The resulting solution was dried over $MgSO_4$ and evaporated. The residue was crystallized from DIPE/$CH_3CN$. After several crystallizations (±)-trans-1-(phenyl-methyl)-3-hydroxy-4-piperidinemethanol was obtained (Yield: 50.1%)

b) A mixture of (±)-trans-1-(phenylmethyl)-3-hydroxy-4-piperidinemethanol (17.8 g, 0.085 mol) (already described in *J. Med. Chem.*, 16, pp. 156-159 (1973)) in methanol (250 ml) was hydrogenated, at 50° C., with palladium on activated carbon (10%, 2 g) as catalyst. After uptake of $H_2$ (1 equivalent), the catalyst was filtered off and the filtrate was evaporated, yielding 12 g of (±)-trans-3-hydroxy-4-piperidinemethanol (interm. 1-a) (used in next reaction step without further purification). The corresponding cis-isomer is known from *J. Org. Chem.*, 34, pp. 3674-3676 (1969).

c) A mixture of intermediate (1-a) (0.086 mol) in DCM (250 ml) was stirred at room temperature. A solution of di-tert-butyl dicarbonate (BOC-anhydride) (0.086 mol) in DCM (50 ml) was added dropwise and the resulting reaction mixture was stirred at room temperature. An oil precipitated. Methanol (60 ml) was added and the resulting reaction solution was stirred for 60 min at room temperature. The solvent was evaporated. The residue was crystallized from DIPE. The precipitate was filtered off and dried, yielding 13.7 g (68.8%) of 1,1-dimethylethyl(trans)-3-hydroxy-4-(hydroxy-methyl)-1-piperidinecarboxylate (intermediate 1-b).

d) Intermediate (1-b) (0.087 mol) was dissolved in chloroform (400 ml) and pyridine (7.51 ml). The solution was cooled to 0° C. 4-Methyl-benzenesulfonyl chloride (0.091 mol) was added portionwise over 20 minutes. The reaction mixture was stirred and refluxed for 16 hours. More 4-methyl-benzenesulfonyl chloride (1.7 g) and pyridine (1.4 ml) were added and the resulting reaction mixture was stirred and refluxed for 6 hours, then cooled, washed with citric acid (10% w/w in $H_2O$), washed with brine, dried, filtered and the solvent was evaporated. The residue was purified by flash column chromatography over silica gel (eluent: DCM). The desired fractions were collected and the solvent was evaporated, yielding 9 g of (intermediate 1-c) as a colourless oil. Intermediate (1-c) (0.13 mol) was separated into its enantiomers by chiral column chromatography over a dynamic axial compression column with Chiralcel AD (20 µm, 100 Å, code 061347) (room temperature, column diameter: 11 cm; eluent: hexane/ethanol 80/20; 50 g product in 5 liters of eluent). Two fraction groups were collected and their solvent was evaporated, yielding 26.2 g of a first eluting fraction fraction (I) and 26 g of a second eluting fraction (II). Fraction (I) was crystallized from DIPE, filtered off and dried, yielding 12.5 g of (+)-1,1-dimethylethyl(trans)-3-hydroxy-4-[[(4-methylphenyl)sulfonyl]oxymethyl]-1-piperidinecarboxylate [intermediate (1-c-I); $[\alpha]_D^{20}$=+13.99° (c=27.87 mg/5 ml in $CH_3OH$)].

Fraction (II) was crystallized from DIPE, filtered off and dried, yielding 15 g of (−)-1,1-dimethylethyl(trans)-3-hydroxy-4-[[(4-methylphenyl)sulfonyl]oxymethyl]-1-piperidinecarboxylate [intermediate (1-c-II); $[\alpha]_D^{20}$=−38.46° (c=25.35 mg/5 ml in $CH_3OH$)].

e) A mixture of intermediate (1-c) (0.023 mol) and benzylamine (0.084 mol) in THF (100 ml) was stirred for 16 hours at 125° C. (autoclave). The reaction mixture was cooled. The solvent was evaporated. The residue was partitioned between DCM and an aqueous $K_2CO_3$ solution. The organic layer was separated, dried, filtered and the solvent was evaporated, yielding 15.4 g of 1,1-dimethylethyl(trans)-3-hydroxy-4-[[(phenylmethyl)amino]methyl]-1-piperidinecarboxylate (intermediate 1-d).

f) A mixture of intermediate (1-d) (max. 0.023 mol crude residue) in methanol (100 ml) was hydrogenated with palladium-on-carbon (10%, 1 g) as a catalyst. After uptake of $H_2$ (1 equivalent), the catalyst was filtered off and the filtrate was evaporated. The residue was solidified in DIPE+ACN, filtered off and dried (vacuum, 40° C.), yielding 4 g (76%) of 1,1-dimethylethyl(trans)-4-(aminomethyl)-3-hydroxy-1-piperidine-carboxylate (intermediate 1-e, mp. 178° C.).

In an analogous way, but starting from cis-3-hydroxy-4-piperidinemethanol (described in *J. Org. Chem.*, 34, pp. 3674-3676 (1969)), 1,1-dimethylethyl(cis)-4-(aminomethyl)-3-hydroxy-1-piperidinecarboxylate (interm. 1-f) was prepared.

Example A.3 a) $CaCO_3$ (3.9 g) was added to a mixture of 1,3-benzodioxol-4-amine (4.11 g) in DCM (40 ml) and $CH_3OH$ (20 ml). This mixture was stirred at room temperature. N,N,N-trimethyl benzenemethanaminium dichloroiodate (11.5 g) was added portionwise at room temperature. The resulting reaction mixture was stirred for 15 minutes at room temperature. The mixture was diluted with water. The layers were separated. The aqueous phase was extracted with DCM. The combined organic layers were washed with water, dried, filtered and the solvent evaporated. The residue was purified by column chromatography over silica gel (eluent: $CH_2Cl_2$/hexane 80/20). The pure fractions were collected and the solvent was evaporated. The residue was crystallized from DIPE. The precipitate was filtered off and dried, yielding 3.5 g (46.9%) of 7-iodo-1,3-benzodioxol-4-amine (intermediate 2-a).

b) Acetic anhydride (14.25 ml) was added dropwise to a mixture of intermediate (2-a) (36.6 g) in acetic acid (500 ml), stirred at room temperature. The reaction mixture was stirred for 15 minutes at room temperature. The reaction mixture was poured out into water (500 ml). The precipitate was filtered, washed with water, then dried, yielding 39.29 g (92.6%) of N-(7-iodo-1,3-benzodioxol-4-yl)acetamide (intermediate 2-b).

c) A mixture of intermediate (2-b) (38.8 g), potassium acetae (20 g) and Pd/C (10%; 2 g) in $CH_3OH$ (500 ml) was stirred at 150° C. under $4.9 \times 10^6$ Pa (50 kg) pressure of CO, during 16 hours. The reaction mixture was cooled, filtered over dicalite, and the filtrate was evaporated. The residue was diluted with water, then extracted three times with DCM. The combined organic layers were dried, filtered and the solvent evaporated. The residue was dissolved in acetic acid (250 ml) and acetic anhydride (6 ml) was added dropwise. The mixture was stirred for 30 minutes at room temperature, then diluted with water (250 ml) and the resulting precipitate was filtered off, washed with water, then dried, yielding 19.4 g (64.7%) of methyl 7-(acetylamino)-1,3-benzodioxole-4-carboxylate (intermediate 2-c).

d) A mixture of intermediate (2-c) (18.5 g) and NCS (11.4 g) in ACN (130 ml) was stirred and refluxed for one hour. The reaction mixture was cooled. The precipitate was filtered off, washed with ACN, with DIPE, then dried, yielding 18.2 g (87%) of methyl 7-(acetylamino)-6-chloro-1,3-benzodioxole-4-carboxylate (intermediate 2-d).

e) Intermediate (2-d) (18.2 g) was added to a solution of KOH (37.6 g) in water (380 ml). The resulting reaction mixture was stirred and refluxed for 3 hours. The mixture was cooled, acidified with hydrochloric acid, and the resulting precipitate was filtered off, washed with water, suspended in ACN, filtered off, then dried, yielding 14 g (>95%) of 7-amino-6-chloro-1,3-benzodioxole-4-carboxylic acid (intermediate 2-e). In an analogous way, 3,4-dihydro-9-iodo-2H-1,5-benzodioxepin-6-amine (intermediate 2-f) was prepared.

Example A.4

A mixture of intermediate (2-e) (1 g) and 1,1'-carbonylbis-1H-imidazole (0.8 g) in ACN (80 ml) was stirred for 3 hours at room temperature. The solvent was evaporated. The residue was partitioned between water and DCM. The organic layer was separated, dried, filtered and the solvent was evaporated. The residue was suspended in DIPE, filtered off, then dried (vacuum), yielding 0.8 g (75%) of 1-[(7-amino-6-chloro-1,3-benzodioxol-4-yl)carbonyl]-1H-imidazole (intermediate 3-a).

N-[4-amino-5-chloro-2,3-dihydro-2,2-dimethyl-7-benzofurancarboyl]-1H-imidazole (intermediate 3-b).

In a similar manner were also prepared:

N-[4-amino-5-chloro-2,3-dihydro-7-benzofuranoyl]-1H-imidazole (interm. 3-c),

N-[8-chloro-3,4-dihydro-9-acetylamino-2H-1,5-benzdiazepine-6-oyl]-1H-imidazole (interm. 3-d), and 1-[(5-amino-6-chloro-3,4-dihydro-2H-1-benzopyran-8-yl) carbonyl]-1H-imidazole (interm. 3-e).

Example A.5

A mixture of intermediate (1-f) (0.09 mol) and intermediate (3-c) (0.087 mol) in ACN (600 ml) was stirred and refluxed for 1 hour. The reaction mixture was cooled to 0° C., and the solvent was evaporated. The residue was partitioned between DCM and water. The organic layer was separated, dried, filtered and the solvent was evaporated. The residue was purified by column chromatography over silica gel (eluent: $CH_2Cl_2/(CH_3OH/NH_3)$ 97/3). The pure fractions were collected and the solvent was evaporated. The residue was crystallized from ACN. The precipitate was filtered off and dried), yielding 28.7 g (78%) of (±)-1,1-dimethylethyl cis-4-[[[(4-amino-5-chloro-2,3-dihydro-7-benzofuranyl)carbonyl] amino]methyl]-3-hydroxy-1-piperidine-carboxylate (interm. 4, mp. 218° C.).

Example A.6

A mixture of intermediate (4) (0.065 mol) in HCl/2-propanol (120 ml) and methanol (1000 ml) was stirred and refluxed for 30 minutes. The reaction mixture was cooled and the solvent was evaporated. The residue was partitioned between DCM and $NH_3$ saturated aqueous NaCl solution. The organic layer was separated, dried, filtered and the solvent was evaporated. The residue was dissolved in 2-propanol and converted into the hydrochloric acid salt (1:2) with HCl/2-propanol. The precipitate was filtered off and dried, yielding 14.6 g (64%) of (cis)-4-amino-5-chloro-2,3-dihydro-N-[(3-hydroxy-4-piperidinyl)methyl]-7-benzofurancarboxamide dihydrochloride (interm. 10, mp. 280° C.).

Example A.7 a) To a stirred and cooled mixture of ethyl 4-oxo-1-piperidinecarboxylate (85.5 g), nitromethane (33.6 g) in methanol (240 ml), sodium methoxide (10 g) is added dropwise. Upon completion, stirring is continued for 2 hours at about 10° C. and further overnight at room temperature. The reaction mixture is evaporated at room temperature, crushed ice is added to the oily residue and the whole is acidified with acetic acid. The product is extracted with trichloromethane, the extract is dried, filtered and evaporated. The oily residue solidifies on triturating in petroleumether. The product is filtered off and dried, yielding 73 g of ethyl 4-hydroxy-4-(nitromethyl)-1-piperidinecarboxylate (interm. 5).

b) A mixture of intermediate (5) (73 g), methanol (400 ml) and acetic acid (150 ml) is hydrogenated in a Parr-apparatus with palladium-on-carbon (10%, 5 g). After the calculated amount of hydrogen is taken up, the catalyst is filtered off and the filtrate is evaporated. To the residue is added crushed ice and the whole is alkalized with potassium hydroxide. The aqueous phase is salted out with potassium carbonate and the product is extracted with benzene. The extract is dried, filtered and evaporated, yielding 63.5 g of ethyl 4-(aminomethyl)-4-hydroxy-1-piperidinecarboxylate (interm. 6, mp. 82° C.).

Example A.8 a) Intermediate (1-d) was purified and separated into its enantiomers by chiral column chromatography over Chiralcel AD (column no: AD2000; type: DAC; 20 μm, 1000 Å; column diameter: 11 cm; eluent: hexane/ethanol 80/20 injection: 1 g/200 ml). Two pure fraction groups were collected and their solvent was evaporated. The first eluting fraction, the (A)-residue, yielded 1,1-dimethylethyl (trans)-3-hydroxy-4-[[(phenylmethyl)amino]-methyl]-1-piperidinecarboxylate (intermediate 25).

b) A mixture of intermediate (25) (0.56 mol) in methanol (700 ml) was hydrogenated at 50° C. with palladium-on-carbon (5 g; 10%) as a catalyst. After uptake of hydrogen (1 equivalent), the catalyst was filtered off and the filtrate was evaporated. The residue was solidified in DIPE, filtered off and dried, yielding 119 g (100%) of (+)-1,1-dimethylethyl (trans)-4-(aminomethyl)-3-hydroxy-1-piperidinecarboxylate (intermediate 2-g; $[\alpha]_D^{20}$=+2.43° (c=24.70 mg/5 ml in $CH_3OH$)).

c) A mixture of intermediate (3-b) (0.62 mol) and intermediate (2-g) (0.62 mol) in ACN (4300 ml) was stirred and refluxed for 90 minutes. The solvent was evaporated. The residue was partitioned between water (1000 ml) and ethyl acetate (4000 ml). The layers were separated. The water layer was extracted once more with ethyl acetate (1000 ml). The combined organic layers were washed with water (2×500 ml), dried, filtered over silica gel and the solvent was evaporated. 2-Propanol was added, then evaporated again, yielding 310 g (quantitative yield; used in next reaction step, without further purification) of 1,1,-dimethylethyl(trans)-4-[[[(4-amino-5-chloro-2,3-dihydro-2,2-dimethyl-7-benzofuranyl)carbonyl]amino]methyl]-3-hydroxy-1-piperidinecarboxylate (intermediate 26).

d) A mixture of intermediate (26) (0.011 mol) in a mixture of HCl in 2-propanol (12 ml) and methanol (100 ml) was stirred and refluxed for 30 minutes. The mixture was cooled and the solvent was evaporated. The residue was partitioned between water/$NH_3$ and DCM. The organic layer was separated, dried, filtered and the solvent was evaporated, yielding 2.84 g (73%) of (−)-(trans)-4-amino-5-chloro-2,3-dihydro-N-[(3-hydroxy-4-piperidinyl)methyl]-2,2-dimethyl-7-benzofurancarboxamide (interm. 14). A sample (0.5 g) was crystallized from ACN with a drop of water, filtered off and dried, yielding 0.2 g of intermediate (14) [mp. 116° C.; $[\alpha]_D^{20}$=−15.91° (c=25.14 mg/5 ml in $CH_3OH$)].

In this manner and in a similar manner were prepared:

TABLE I-1

| Int. No. | Ex. No. | R¹, R² (benzofused ring) | OR⁴ | Physical data mp. in ° C. |
|---|---|---|---|---|
| 10 | A.6 | Cl, 2,3-dihydrobenzofuran (7-methyl) | OH | cis; .2HCl; mp. 280 |
| 11 | A.6 | Cl, 2,3-dihydrobenzofuran (7-methyl) | OH | trans; mp. 198° C. |
| 12 | A.6 | Cl, methylenedioxy (7-methyl) | OH | trans |
| 13 | A.6 | Cl, 2,2-dimethyl-2,3-dihydrobenzofuran (7-methyl) | OH | trans; .HCl .H₂O |

TABLE I-1-continued

| Int. No. | Ex. No. | R¹, R² (benzofused ring) | OR⁴ | Physical data mp. in ° C. |
|---|---|---|---|---|
| 14 | A.8 | Cl, 2,2-dimethyl-2,3-dihydrobenzofuran (7-methyl) | OH | (A)-trans; $[\alpha]_D^{20}$ = −15.91° (c = 25.14 mg/5 ml in $CH_3OH$) |
| 15 | A.6 | Cl, 1,4-dioxane-fused (7-methyl) | OH | cis |
| 16 | A.6 | Cl, 1,4-dioxane-fused (7-methyl) | OH | cis; .2HCl; mp. 242° C. |
| 17 | A.6 | Cl, 1,4-dioxane-fused (7-methyl) | OH | trans; mp. 190° C. |
| 18 | A.6 | Cl, 1,4-dioxepane-fused (7-methyl) | OH | trans; .2HCl; mp. 180° C. |

TABLE I-1-continued

Structure: H-N(piperidine with OR⁴ at 3-position)-CH₂-N(H)-C(=O)-benzene(R³, R¹, R², NH₂)

Aniline substructure: methyl-benzene(R³, R¹, R²)-NH₂

| Int. No. | Ex. No. | R¹, R², R³ (aniline) | OR⁴ | Physical data mp. in ° C. |
|---|---|---|---|---|
| 19 | A.6 | 5-chloro-8-methyl-chroman-4-amine | OH | trans; .H₂O; mp. 130° C. |
| 20 | A.6 | 5-chloro-7-methyl-2,3-dihydrobenzofuran-4-amine | OCH₃ | cis |

.C₃H₈O stands for the 2-propanolate salt

TABLE I-2

Structure: H-N(piperidine with OR⁴ at 4-position)-CH₂-N(H)-C(=O)-benzene(R³, R¹, R², NH₂)

Aniline substructure: methyl-benzene(R³, R¹, R²)-NH₂

| Int. No. | Ex. No. | R¹, R², R³ (aniline) | OR⁴ | Physical data mp. in ° C. |
|---|---|---|---|---|
| 21 | A.6 | 5-chloro-7-methyl-2,3-dihydrobenzofuran-4-amine | OH | mp. 205° C. |
| 22 | A.6 | 5-chloro-7-methyl-2,2-dimethyl-2,3-dihydrobenzofuran-4-amine | OH | — |
| 23 | A.6 | 5-chloro-7-methyl-2,2-dimethyl-2,3-dihydrobenzofuran-4-amine | OCH₃ | — |
| 24 | A.6 | 5-chloro-7-methyl-2,2-dimethyl-2,3-dihydrobenzofuran-4-amine | OCH₃ | .1/2C₂H₂O₄ |

.C₂H₂O₄ stands for the ethanedioate salt

B. Preparation of the Final Compounds

Example B.1

A mixture of intermediate (10) (0.019 mol), 2-(3-chloropropyl)-2-methyl-1,3-dioxolane (0.029 mol), sodium carbonate (0.076 mol) and potassium iodide (catalytic quantity) in MIK (300 ml, dried over MgSO₄) was stirred and refluxed for 48 hours. The reaction mixture was cooled, filtered and the filtrate was evaporated. The residue was purified by column chromatography over silica gel (eluent: CH₂Cl₂/(CH₃OH/NH₃) 95/5). The pure fractions were collected and the solvent was evaporated. The residue was solidified in DIPE (0° C.), filtered off and dried, yielding 5.5 g (64%) of (cis)-4-amino-5-chloro-2,3-dihydro-N-[[3-hydroxy-1-[3-(2-methyl-1,3-dioxolan-2-yl)propyl]-4-piperidinyl]methyl]-7-benzofuran-carboxamide (comp. 7, mp. 118° C.).

Example B.2

A mixture of intermediate (17) (0.006 mol) and butyraldehyde (0.014 mol) in methanol (150 ml) was hydrogenated with platina-on-carbon (5%, 1 g) as a catalyst in the presence of thiophene (4%, 1 ml). After uptake of hydrogen gas (1 equivalent), the catalyst was filtered off and the filtrate was evaporated. The residue was purified by column chromatography over silica gel (eluent: $CH_2Cl_2/(CH_3OH/NH_3)$ 95/5). The pure fractions were collected and the solvent was evaporated. The residue was solidified in DIPE+ACN. The precipitate was filtered off and dried, yielding 0.53 g of (trans)-8-amino-N-[(1-butyl-3-hydroxy-4-piperidinyl)methyl]-7-chloro-2,3-dihydro-1,4-benzodioxin-5-carboxamide (comp. 55, mp. 122° C.).

Example B.3

A mixture of compound (7) (0.008 mol) in HCl (8 ml) and THF (80 ml) was stirred and refluxed for one hour. The reaction mixture was cooled, then alkalized with $NH_3/CH_3OH$ (until pH=14). DCM was added. The organic layer was separated, dried, filtered and the solvent was evaporated. The residue was purified by column chromatography over silica gel (eluent: $CH_2Cl_2/(CH_3OH/NH_3)$ 95/5). The desired fractions were collected and the solvent was evaporated. The residue was crystallized from ACN. The precipitate was filtered off and dried, yielding 1.7 g of (cis)-4-amino-5-chloro-2,3-dihydro-N-[[3-hydroxy-1-(4-oxopentyl)-4-piperidinyl]methyl]-7-benzo-furancarboxamide (comp. 4, mp. 118° C.).

Example B.4

Compound (38) (10 g) was purified and separated into its enantiomers by chiral column chromatography over Chiralcel AS (20 μm, 1000 Å; eluent: hexane/2-propanol 80/20; injection: 1 g/200 ml). Two pure fraction groups were collected and their solvent was evaporated. The (A)-residue was crystallized from DIPE with a small amount of ACN and a little water. The precipitate was filtered off, washed, and dried, yielding 3.5 g of trans-(−)-4-amino-5-chloro-2,3-dihydro-N-[[3-hydroxy-1-(3-methoxypropyl)-4-piperidinyl]methyl]-2,2-dimethyl-7-benzofurancarboxamide [compound 39, mp. 96° C.; $[\alpha]_D^{20}$=−12.29° (c=0.5% in $CH_3OH$)]. The absolute configuration was determined to be (3S,4S).

The (B)-residue was crystallized from DIPE with a small amount of ACN and a little water. The precipitate was filtered off, washed, and dried, yielding 3.6 g of trans-(+)-4-amino-5-chloro-2,3-dihydro-N-[[3-hydroxy-1-(3-methoxypropyl)-4-piperidinyl]-methyl]-2,2-dimethyl-7-benzofurancarboxamide[compound 40, mp. 97° C.; $[\alpha]_D^{20}$=+12.72° (c=0.5% in $CH_3OH$)].

Example B.5

A mixture of compound (76) (0.015 mol) in $CH_3OH/NH_3$ (250 ml) was hydrogenated at 10° C. with Raney nickel (3 g) as a catalyst. After uptake of hydrogen (2 equivalents), the catalyst was filtered off over dicalite and the filtrate was evaporated, yielding 5.7 g of (±)-trans-5-amino-N-[[1-(2-aminoethyl)-3-hydroxy-4-piperidinyl]methyl]-6-chloro-3,4-dihydro-2H-1-benzopyran-8-carboxamide (compound 82).

Table F-1 to F-8 list the compounds that were prepared according to one of the above Examples.

TABLE F-1

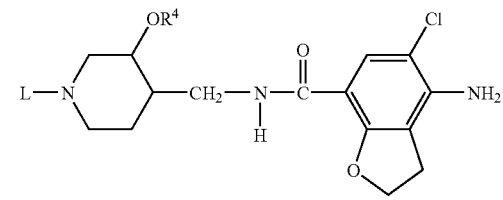

| Co. No. | Ex. No. | -L | $OR^4$ | Physical data |
|---|---|---|---|---|
| 1 | B.2 | $CH_3(CH_2)_3$— | OH | cis, mp. 126° C. |
| 2 | B.2 | $CH_3(CH_2)_3$— | OH | trans, mp. 149° C. |
| 3 | B.1 | $CH_3O(CH_2)_3$— | OH | trans, mp. 136° C. |
| 4 | B.3 | $CH_3CO(CH_2)_3$— | OH | cis, mp. 118° C. |
| 5 | B.3 | $CH_3CO(CH_2)_3$— | OH | trans, mp. 166° C. |
| 6 | B.1 | ![tetrahydrofuran-CH2—] | OH | trans; mp. 162° C. |
| 7 | B.1 | ![dioxolane with CH3 and (CH2)3—] | OH | cis; mp 118° C. |
| 8 | B.1 | ![dioxolane with CH3 and (CH2)3—] | OH | trans |

TABLE F-1-continued

[Structure: L-N(piperidine with OR⁴)-CH₂-NH-C(=O)-[chloro-amino-dihydrobenzofuran]]

| Co. No. | Ex. No. | -L | OR⁴ | Physical data |
|---|---|---|---|---|
| 9 | B.1 | (2-methyl-1,3-dioxolan-2-yl)-(CH₂)₃— | OH | trans; mp. 166° C.; .C₂H₂O₄.C₃H₈O |
| 10 | B.1 | 3-methyl-6-oxopyridazin-1-yl-(CH₂)₂— | OH | trans; mp. 210° C. |
| 11 | B.1 | 3-chloro-6-oxopyridazin-1-yl-(CH₂)₃— | OH | trans; mp. 180° C. |
| 12 | B.1 | 3-chloro-6-oxopyridazin-1-yl-(CH₂)₂— | OH | trans; mp. 210° C. |
| 13 | B.1 | 3-methyl-6-oxopyridazin-1-yl-(CH₂)₃— | OH | trans; mp. 178° C. |
| 14 | B.1 | 1-oxophthalazin-2-yl-(CH₂)₂— | OH | trans; mp. 220° C. |
| 15 | B.1 | 3-ethyl-2-oxo-2,3-dihydro-1H-benzimidazol-1-yl-(CH₂)₃— | OH | trans; mp. 185.4° C. |

TABLE F-1-continued

Structure: L-N(piperidine with OR⁴ at 3-position)-CH(4-position)-CH₂-NH-C(=O)-[benzofuran with Cl at 5, NH₂ at 4, 2,3-dihydro]

| Co. No. | Ex. No. | -L | OR⁴ | Physical data |
|---|---|---|---|---|
| 16 | B.1 | CH₃CH₂-N(C=O)N-(CH₂)₂— (1-ethyl-2-oxo-2,3-dihydro-1H-imidazol-3-yl with ethylene linker) | OH | trans; mp. 120° C; .H₂O |
| 17 | B.1 | HO—(CH₂)₂—O—(CH₂)₂— | OH | trans; mp. 118° C. |
| 18 | B.1 | NC—(CH₂)₃— | OH | trans; mp. 168° C. |
| 19 | B.1 | (CH₃)₂CHO(CH₂)₃— | OH | trans; mp. 119° C. |
| 20 | B.1 | CH₃—SO₂—NH—(CH₂)₂— | OH | trans; mp. 168° C. |
| 21 | B.1 | pyrrolidin-1-yl-C(=O)—(CH₂)₃— | OH | trans; mp. 164° C. |
| 22 | B.1 | (tetrahydrofuran-2-yl)-CH₂— | OCH₃ | trans; mp. 110° C. |
| 23 | B.1 | (tetrahydrofuran-2-yl)-(CH₂)₂— | OH | trans; mp. 144° C. |
| 24 | B.1 | (tetrahydrofuran-2-yl)-(CH₂)₃— | OH | trans; mp. 136° C. |
| 25 | B.1 | (tetrahydropyran-2-yl)-CH₂— | OH | trans, mp. 160° C. |
| 26 | B.1 | (tetrahydropyran-2-yl)-(CH₂)₂— | OH | trans; mp. 166° C. |
| 27 | B.1 | (2-methyl-1,3-dioxolan-2-yl)-(CH₂)₃— | OCH₃ | trans; mp. 130° C. |
| 28 | B.3 | CH₃—CO—(CH₂)₃— | OCH₃ | trans; mp. 130° C. |
| 29 | B.2 | CH₃—(CH₂)₃— | OCH₃ | trans; mp. 130° C. |
| 30 | B.1 | CH₃—O—(CH₂)₃— | OCH₃ | trans; mp. 120° C. |

.C₂H₂O₄ stands for the ethanedioate salt
.C₃H₈O stands for the 2-propanolate salt

TABLE F-2

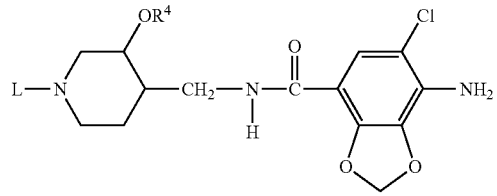

| Co. No. | Ex. No. | -L | OR⁴ | Physical data |
|---|---|---|---|---|
| 31 | B.2 | $CH_3(CH_2)_3$— | OH | trans; mp. 120° C. |
| 32 | B.1 | $CH_3O(CH_2)_3$— | OH | trans; $.H_2O$ |
| 33 | B.3 | $CH_3CO(CH_2)_3$— | OH | trans; mp. 138° C. |
| 34 | B.1 | (dioxolane with $CH_3$ and $(CH_2)_3$—) | OH | trans; mp. 166° C. |

TABLE F-2-continued

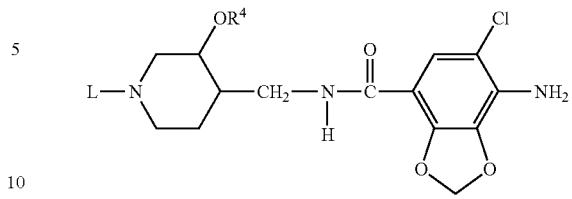

| Co. No. | Ex. No. | -L | OR⁴ | Physical data |
|---|---|---|---|---|
| 35 | B.1 | (dioxolane with $CH_3$ and $(CH_2)_3$—) | OH | trans; $.C_2H_2O_4$; mp. 166° C. |

$.C_2H_2O_4$ stands for the ethanedioate salt

TABLE F-3

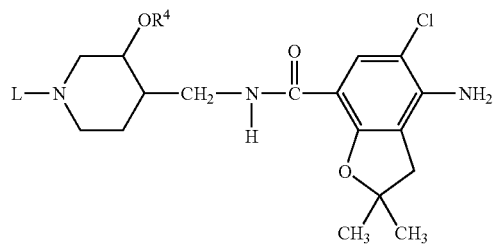

| Co. No. | Ex. No. | -L | OR⁴ | Physical data |
|---|---|---|---|---|
| 36 | B.2 | $CH_3(CH_2)_3$— | OH | trans; mp. 138° C. |
| 37 | B.1 | $CH_3O(CH_2)_3$— | OH | trans; $.C_2H_2O_4$; mp. 197° C. |
| 38 | B.1 | $CH_3O(CH_2)_3$— | OH | trans; mp. 100° C. |
| 39 | B.4 | $CH_3O(CH_2)_3$— | OH | (3S-trans); mp. 96° C.; $[\alpha]_D^{20} = -12.29°$ (c = 0.5% in $CH_3OH$) |
| 40 | B.4 | $CH_3O(CH_2)_3$— | OH | (3R-trans); mp. 97° C.; $[\alpha]_D^{20} = +12.72°$ (c = 0.5% in $CH_3OH$) |
| 56 | B.4 | $CH_3O(CH_2)_3$— | OH | (3S-trans); mp. 251.5° C.; .HCl; $[\alpha]_D^{20} = -11.72°$ (c = 0.5% in $CH_3OH$) |
| 95 | B.4 | $CH_3O(CH_2)_3$— | OH | (3S-trans); $.HCl.H_2O$ |
| 96 | B.4 | $CH_3O(CH_2)_3$— | OH | (3S-trans); $.HBr.H_2O$; mp. 210° C.; $[\alpha]_D^{20} = -10.82°$ (c = 1% in $CH_3OH$) |
| 41 | B.1 | $CH_3O(CH_2)_3$— | OH | cis; mp. 150° C. |
| 42 | B.1 | $(CH_3)_2CHO(CH_2)_3$— | OH | trans; $.(Z)-C_4H_4O_4$ |
| 43 | B.1 | $CH_3CH_2O(CO)(CH_2)_2$— | OH | trans |
| 44 | B.1 | $CH_3CH_2O(CO)(CH_2)_2$— | OH | trans; $.(Z)-C_4H_4O_4$ |
| 45 | B.3 | $HO—CO—(CH_2)_2$— | OH | trans; $.HCl .H_2O$ |
| 46 | B.1 | (tetrahydrofuran-$CH_2$—) | OH | trans; mp. 190° C. |
| 47 | B.1 | (dioxolane with $CH_3$ and $(CH_2)_3$—) | OH | trans |

TABLE F-3-continued

[Structure: piperidine with OR⁴ at 3-position, L on N, CH₂-NH-C(=O) linker to benzofuran with Cl, NH₂, and 2,2-dimethyl-2,3-dihydrobenzofuran core]

| Co. No. | Ex. No. | -L | OR⁴ | Physical data |
|---|---|---|---|---|
| 48 | B.1 | [2-methyl-1,3-dioxolane with (CH₂)₃-]  CH₃  (CH₂)₃— | OH | trans; .C₂H₂O₄; mp. 120° C. |
| 49 | B.3 | CH₃—CO—(CH₂)₃— | OH | trans; mp. 148° C. |
| 50 | B.1 | [6-methyl-3-oxo-pyridazin-2-yl]-(CH₂)₂— | OH | trans; mp. 202° C. |
| 51 | B.2 | CH₃(CH₂)₃— | OCH₃ | trans; .C₂H₂O₄; mp. 132° C. |
| 52 | B.1 | CH₃—O—(CH₂)₃— | OCH₃ | trans; .C₂H₂O₄; mp. 160° C. |
| 53 | B.1 | [2-methyl-1,3-dioxolane with (CH₂)₃-]  CH₃  (CH₂)₃— | OCH₃ | trans; mp. 100° C. |

.C₂H₂O₄ stands for the ethanedioate salt
.(Z)-C₄H₄O₄ stands for (Z)-2-butenedioate salt

TABLE F-4

[Structure: piperidine with OR⁴, L on N, CH₂-NH-C(=O) linker to chloro-amino-2,3-dihydro-1,4-benzodioxine]

| Co. No. | Ex. No. | -L | OR⁴ | Physical data |
|---|---|---|---|---|
| 54 | B.2 | CH₃(CH₂)₃— | OH | cis; .HCl .H₂O; mp. 104° C. |
| 55 | B.2 | CH₃(CH₂)₃— | OH | trans; mp. 122° C. |
| 57 | B.1 | CH₃O(CH₂)₃— | OH | trans; mp. 138° C. |
| 58 | B.3 | CH₃CO(CH₂)₃— | OH | cis; mp. 138° C. |
| 59 | B.3 | CH₃CO(CH₂)₃— | OH | trans; .H₂O |
| 60 | B.1 | [tetrahydrofuran-2-yl]-CH₂— | OH | trans; mp. 140° C. |
| 61 | B.1 | [2-methyl-1,3-dioxolane with (CH₂)₃-]  CH₃  (CH₂)₃— | OH | cis |
| 62 | B.1 | [2-methyl-1,3-dioxolane with (CH₂)₃-]  CH₃  (CH₂)₃— | OH | trans |

TABLE F-4-continued

[Structure: L—N(piperidine with OR⁴)—CH₂—NH—C(=O)—(chloro-amino-benzodioxine)]

| Co. No. | Ex. No. | -L | OR⁴ | Physical data |
|---|---|---|---|---|
| 63 | B.1 | [2-methyl-1,3-dioxolan-2-yl]-(CH₂)₃— | OH | trans; .C₂H₂O₄; mp. 180° C. |
| 64 | B.1 | [6-methyl-3-oxo-pyridazin-2-yl]-(CH₂)₂— | OH | trans; .C₂H₂O₄; mp. 208° C. |

.C₂H₂O₄ stands for the ethanedioate salt

TABLE F-8

[Structure: L—N(piperidine with OR⁴)—CH₂—NH—C(=O)—(chloro-amino-benzodioxepine, 7-membered dioxa ring)]

| Co. No. | Ex. No. | -L | OR⁴ | Physical data |
|---|---|---|---|---|
| 65 | B.2 | CH₃(CH₂)₃— | OH | trans; .HCl; mp. 216° C. |
| 66 | B.1 | CH₃O(CH₂)₃— | OH | trans; .C₂H₂O₄; mp. 176° C. |

TABLE F-8-continued

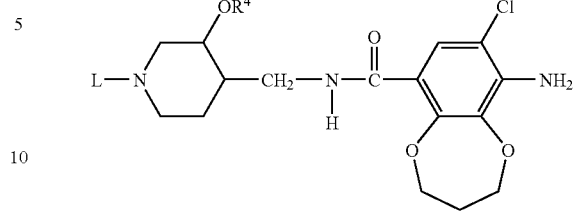

| Co. No. | Ex. No. | -L | OR⁴ | Physical data |
|---|---|---|---|---|
| 67 | B.3 | CH₃CO(CH₂)₃— | OH | trans; mp. 130° C. |
| 68 | B.1 | [tetrahydrofuran-2-yl]-CH₂— | OH | trans; mp. 154° C. |
| 69 | B.1 | [2-methyl-1,3-dioxolan-2-yl]-(CH₂)₃— | OH | trans; mp. 128° C. |
| 70 | B.1 | [6-methyl-3-oxo-pyridazin-2-yl]-(CH₂)₂— | OH | trans; .C₂H₂O₄; mp. 188° C. |

.C₂H₂O₄ stands for the ethanedioate salt

TABLE F-6

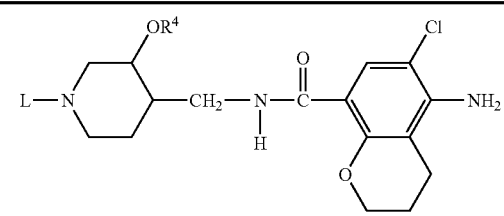

| Co. No. | Ex. No. | -L | OR⁴ | Physical data |
|---|---|---|---|---|
| 71 | B.1 | CH₃—O—(CH₂)₃— | OH | trans; .H₂O; mp. 120° C. |
| 72 | B.1 | [tetrahydrofuran-2-yl]-CH₂— | OH | trans; .H₂O; mp. 120° C. |

TABLE F-6-continued

Structure: L–N(piperidine with OR⁴ at 3-position)–CH₂–NH–C(=O)–[6-chloro-5-amino-chroman-8-yl]

| Co. No. | Ex. No. | -L | OR⁴ | Physical data |
|---|---|---|---|---|
| 73 | B.1 | 2-methyl-1,3-dioxolan-2-yl-(CH₂)₃— | OH | trans; mp. <80° C. |
| 74 | B.1 | HO—(CH₂)₃— | OH | trans; .2H₂O; mp. <100° C. |
| 75 | B.1 | HO—(CH₂)₂—O—(CH₂)₂— | OH | trans; .C₂H₂O₄; mp. 168° C. |
| 76 | B.1 | NC—CH₂— | OH | trans |
| 77 | B.1 | NC—(CH₂)₃— | OH | trans; mp. 156° C. |
| 78 | B.2 | CH₃—(CH₂)₃— | OH | trans; .H₂O; mp. 125° C. |
| 79 | B.1 | cyclopropyl-CH₂— | OH | trans; .H₂O; mp. 115° C. |
| 80 | B.3 | CH₃—CO—(CH₂)₃— | OH | trans; mp. 100° C. |
| 81 | B.1 | (CH₃)₂CH—O—(CH₂)₃— | OH | trans; mp. 100° C. |
| 82 | B.5 | H₂N—(CH₂)₂— | OH | trans |
| 83 | B.1 | 6-oxo-pyridazin-1-yl-(CH₂)₂— | OH | trans; mp. 190° C. |
| 84 | B.1 | 1,3-dimethyl-pyrazin-2-yl-NH-(CH₂)₂— | OH | trans; mp. 175° C. |

.C₂H₂O₄ stands for the ethanedioate salt

TABLE F-7

Structure: L–N(piperidine with OR⁴ at 4-position)–CH₂–NH–C(=O)–[6-chloro-5-amino-2,3-dihydrobenzofuran-7-yl]

| Co. No. | Ex. No. | -L | OR⁴ | Physical data |
|---|---|---|---|---|
| 85 | B.2 | CH₃(CH₂)₃— | OH | mp. 135° C. |
| 86 | B.1 | CH₃O(CH₂)₃— | OH | mp. 130° C. |
| 87 | B.1 | 2-methyl-1,3-dioxolan-2-yl-(CH₂)₃— | OH | mp. 134° C. |
| 88 | B.3 | CH₃—CO—(CH₂)₃— | OH | mp. 165° C. |

TABLE F-8

[Structure: L—N(piperidine with OR⁴ and CH₂)—N(H)—C(=O)—(5-chloro-4-amino-2,2-dimethyl-2,3-dihydrobenzofuran-7-yl)]

| Co. No. | Ex. No. | -L | OR⁴ | Physical data |
|---|---|---|---|---|
| 89 | B.2 | $CH_3(CH_2)_3-$ | OH | mp. 174° C.; $.C_2H_2O_4$ |
| 90 | B.1 | $CH_3O(CH_2)_3-$ | OH | mp. 143° C.; $.C_2H_2O_4$ |
| 91 | B.1 | (tetrahydrofuran-2-yl)-CH₂— | OH | mp. 174° C; $.C_2H_2O_4$ |
| 92 | B.1 | 2-methyl-2-propyl-1,3-dioxolane, $CH_3, (CH_2)_3-$ | OH | mp. 128° C. |
| 93 | B.3 | $CH_3-CO-(CH_2)_3-$ | OH | mp. 130° C. |
| 94 | B.1 | $HO-(CH_2)_2-O-(CH_2)_2-$ | OH | mp. 115° C.; $.(E)-C_4H_4O_4$ |

$.C_2H_2O_4$ stands for the ethanedioate salt
$.(E)-C_4H_4O_4$ stands for the (E)-2-butenedioate salt

C. Pharmacological Examples

C.1. Gastric Emptying of an Acaloric Liquid Test Meal Delayed by Administration of Lidamidine, in Conscious Dogs Female beagle dogs, weighing 7-14 kg, were trained to stand quietly in Pavlov frames. They were implanted with a gastric cannula under general anesthesia and aseptic precautions. After a median laparatomy, an incision was made through the gastric wall in the longitudinal direction between the greater and the lesser curve, 2 cm above the nerves of Latarjet. The cannula was secured to the gastric wall by means of a double purse string suture and brought out via a stab wound at the left quadrant of the hypochondrium. Dogs were allowed a recovery period of at least two weeks. Experiments were started after a fasting period of 24 hours, during which water was available ad libitum. At the beginning of the experiment, the cannula was opened in order to remove any gastric juice or food remnants.

The stomach was cleansed with 40 to 50 ml lukewarm water. The test compound was administered I.V. (in a volume≦3 ml via the vena cephalica), S.C. (in a volume≦3 ml) or P.O. (in a volume of 1 ml/kg body weight, applied intragastrically via the cannula with a device that filled the lumen of the cannula; after injection of the test compound, 5 ml NaCl 0.9% was injected in order to correct for the dead space in the injection system). Immediately after administration of the test compound or its solvent, lidamidine 0.63 mg/kg was administered subcutaneously. 30 min later, the cannula was opened to determine the amount of fluid present in the stomach, promptly followed by reintroduction of the fluid. Then the test meal was administered via the cannula. This test meal consisted of 250 ml distilled water containing glucose (5 g/l) as a marker. The cannula remained closed for 30 min, whereafter the gastric contents were drained from the stomach to measure total volume (t=30 min). For later analysis 1 ml of the gastric contents was taken, promptly followed by reintroduction of the rest volume into the stomach. This sequence was repeated 4 times with 30 min intervals (t=60, 90, 120, 150 min).

In the 1 ml samples of the gastric contents, the glucose concentrations were measured on a Hitachi 717 automatic analyzer by the hexokinase method (Schmidt, 1961). These data were used to determine the absolute amount of glucose that remained in the stomach after each 30 min period, as a measure for the rest volume of the meal itself, independent of acid secretion.

Curves were fitted to the measurement points (glucose versus time) using weighed non-linear regression analysis. Gastric emptying was quantified as the time needed to empty 70% of the meal ($^t$ 70%). The control emptying time was calculated as the mean $^t$ 70% of the last 5 solvent experiments of the same dog. Acceleration of delayed gastric emptying (Δt) was calculated as the time difference between $^t$ 70% compound and $^t$ 70% solvent. To correct for variations in emptying rate between dogs, Δt was expressed as % of $^t$ 70% solvent (Schuurkes et al, 1992)).

TABLE C-1

The acceleration of gastric emptying of a liquid meal delayed by lidamidine in conscious dog was measured for the following compounds at a dose of 0.01 mg/kg (column $\Delta T/T^a$) and 0.0025 mg/kg (column $\Delta T/T^b$).

| Co. No. | $\Delta T/T^a$ | $\Delta T/T^b$ |
|---|---|---|
| 1 | −0.20 | −0.23 |
| 2 | −0.34 | −0.61 |
| 3 | −0.73 | −0.51 |
| 4 | −0.08 | −0.21 |
| 5 | −0.36 | −0.57 |

TABLE C-1-continued

The acceleration of gastric emptying of a liquid meal delayed by lidamidine in conscious dog was measured for the following compounds at a dose of 0.01 mg/kg (column $\Delta T/T^a$) and 0.0025 mg/kg (column $\Delta T/T^b$).

| Co. No. | $\Delta T/T^a$ | $\Delta T/T^b$ |
|---|---|---|
| 6 | −0.52 | −0.52 |
| 7 | 0.11 | −0.07 |
| 9 | −0.52 | −0.24 |
| 10 | −0.11 | −0.15 |
| 11 | −0.45 | −0.19 |
| 12 | −0.01 | −0.03 |
| 14 | −0.28 | — |
| 15 | −0.04 | −0.23 |
| 16 | −0.08 | −0.17 |
| 17 | 0.06 | −0.30 |
| 18 | −0.57 | −0.47 |
| 19 | −0.78 | −0.30 |
| 20 | −0.28 | −0.20 |
| 21 | −0.15 | −0.21 |
| 22 | −0.58 | −0.37 |
| 23 | −0.53 | −0.15 |
| 24 | 0.01 | −0.13 |
| 25 | −0.63 | −0.38 |
| 26 | −0.56 | — |
| 27 | −0.49 | −0.40 |
| 28 | −0.56 | −0.42 |
| 29 | −0.51 | −0.32 |
| 30 | −0.59 | −0.55 |
| 36 | −0.01 | — |
| 37 | −0.62 | −0.41 |
| 39 | −0.53 | −0.43 |
| 40 | −0.22 | −0.17 |
| 42 | −0.12 | — |
| 46 | −0.43 | — |
| 49 | −0.28 | −0.19 |
| 51 | −0.45 | — |
| 52 | −0.18 | — |
| 53 | −0.47 | — |
| 54 | −0.28 | 0.04 |
| 55 | −0.29 | −0.18 |
| 57 | −0.10 | −0.03 |
| 58 | 0.09 | −0.20 |
| 59 | −0.13 | −0.15 |
| 63 | −0.07 | 0.12 |
| 64 | −0.03 | −0.32 |
| 65 | −0.07 | — |
| 72 | −0.47 | 0.08 |
| 73 | −0.52 | −0.48 |
| 74 | −0.51 | — |
| 75 | −0.01 | −0.39 |
| 76 | −0.18 | — |
| 77 | −0.18 | — |
| 78 | −0.50 | −0.33 |
| 79 | −0.34 | — |
| 80 | −0.51 | −0.11 |
| 81 | −0.16 | — |
| 84 | −0.40 | — |
| 86 | −0.47 | −0.33 |
| 87 | −0.28 | — |
| 91 | −0.16 | — |
| 92 | −0.45 | — |
| 93 | −0.03 | — |

TABLE C-2

The acceleration of gastric emptying of a liquid meal delayed by lidamidine in conscious dog was measured for the following intermediates at a dose of 0.01 mg/kg (column $\Delta T/T^a$) and 0.0025 mg/kg (column $\Delta T/T^b$).

| Intm. No. | $\Delta T/T^a$ | $\Delta T/T^b$ |
|---|---|---|
| 10 | −0.28 | −0.04 |
| 11 | −0.10 | 0.03 |
| 13 | 0.18 | — |
| 17 | −0.28 | −0.18 |

The invention claimed is:

1. A compound of formula (I)

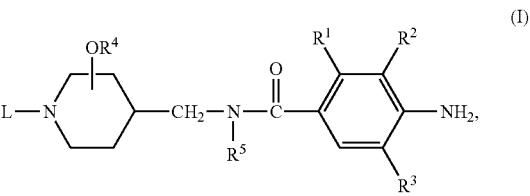

a stereochemically isomeric form thereof, an N-oxide form thereof or a pharmaceutically acceptable acid or base addition salt thereof, wherein $R^1$ and $R^2$ taken together form a bivalent radical of formula —O—CH$_2$—CH$_2$—     (a-2), wherein in said bivalent radicals one or two hydrogen atoms may be substituted with $C_{1-6}$alkyl, $R^3$ is hydrogen or halo;
$R^4$ is hydrogen or $C_{1-6}$alkyl;
$R^5$ is hydrogen or $C_{1-6}$alkyl;
L is $C_{3-6}$cycloalkyl, $C_{5-6}$cycloalkanone, or $C_{2-6}$alkenyl, or L is a radical of formula -Alk-R$^6$     (b-1), -Alk-X—R$^7$     (b-2), -Alk-Y—C(=O)—R$^9$     (b-3), or -Alk-Y—C(=O)—NR$^{11}$R$^{12}$     (b-4), wherein each Alk is $C_{1-12}$alkanediyl; and
$R^6$ is hydrogen, hydroxy, cyano, $C_{1-6}$alkylsulfonylamino, $C_{3-6}$cycloalkyl, $C_{5-6}$cyclo-alkanone, or Het$^1$;
$R^7$ is hydrogen, $C_{1-6}$alkyl, hydroxyC$_{1-6}$alkyl, $C_{3-6}$cycloalkyl, or Het$^2$;
X is O, S, SO$_2$ or NR$^8$; said R$^8$ being hydrogen or $C_{1-6}$alkyl;
$R^9$ is hydrogen, $C_{1-6}$alkyl, $C_{3-6}$cycloalkyl, $C_{1-6}$alkyloxy or hydroxy;
Y is NR$^{10}$ or a direct bond; said R$^{10}$ being hydrogen or $C_{1-6}$alkyl;
$R^{11}$ and $R^{12}$ each independently are hydrogen, $C_{1-6}$alkyl, $C_{3-6}$cycloalkyl, or R$^{11}$ and R$^{12}$ combined with the nitrogen atom bearing R$^{11}$ and R$^{12}$ may form a pyrrolidinyl or piperidinyl ring both being optionally substituted with $C_{1-6}$alkyl, amino or mono or di($C_{1-6}$alkyl)amino, or said R$^{11}$ and R$^{12}$ combined with the nitrogen bearing R$^{11}$ and R$^{12}$ may form a piperazinyl or 4-morpholinyl radical both being optionally substituted with $C_{1-6}$alkyl; and
Het$^1$ and Het$^2$ each independently are selected from furan; furan substituted with $C_{1-6}$alkyl or halo; tetrahydrofuran; a tetrahydrofuran substituted with $C_{1-6}$alkyl; a dioxolane; a dioxolane substituted with $C_{1-6}$alkyl, a dioxane; a dioxane substituted with $C_{1-6}$alkyl; tetrahydropyran; a tetrahydropyran substituted with $C_{1-6}$alkyl; pyrrolidinyl; pyrrolidinyl substituted with one or two substituents each independently selected from halo, hydroxy, cyano, or $C_{1-6}$alkyl; pyridinyl; pyridinyl substituted with one or two substituents each independently selected from halo, hydroxy, cyano, $C_{1-6}$alkyl; pyrimidinyl; pyrimidinyl substituted with one or two substituents each independently selected from halo, hydroxy, cyano, $C_{1-6}$alkyl, $C_{1-6}$alkyloxy, amino and mono and di($C_{1-6}$alkyl) amino; pyridazinyl; pyridazinyl substituted with one or two substituents each independently selected from hydroxy, $C_{1-6}$alkyloxy, $C_{1-6}$alkyl or halo; pyrazinyl; pyrazinyl substituted with one ore two substituents each independently selected from halo, hydroxy, cyano, $C_{1-6}$alkyl, $C_{1-6}$alkyloxy, amino, mono- and di($C_{1-6}$alkyl)amino and $C_{1-6}$alkyloxycarbonyl;

Het$^1$ can also be a radical of formula

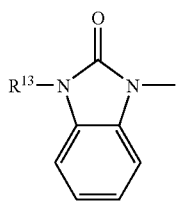
(c-1)

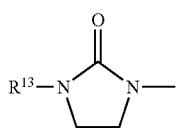
(c-2)

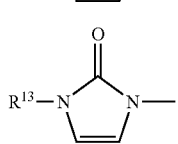
(c-3)

(c-4)

Het$^1$ and Het$^2$ each independently can also be selected from the radicals of formula

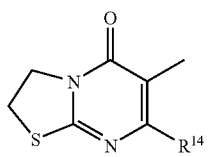
(d-1)

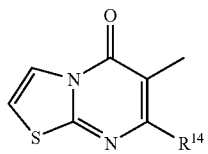
(d-2)

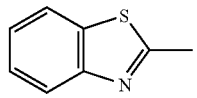
(d-3)

$R^{13}$ and $R^{14}$ each independently are hydrogen or $C_{1-4}$alkyl; and wherein the —OR$^4$ is situated at the 2 or 3 position of the central piperidine moiety.

2. The compound as claimed in claim 1 wherein the —OR$^4$ radical has the transconfiguration.

3. The compound as claimed in claim 1 wherein L is $C_{3-6}$cycloalkyl or $C_{2-6}$alkenyl; or L is a radical of formula (b-1), wherein each Alk is $C_{1-6}$alkanediyl, and R$^6$ is hydrogen, hydroxy, cyano, amino, $C_{1-6}$alkylsulfonylamino, $C_{3-6}$cycloalkyl or Het$^1$, wherein Het$^1$ is tetrahydrofiaran; dioxolane; dioxolane substituted with $C_{1-6}$alkyl; tetrahydropyran; pyridazinyl substituted with one or more substituents selected from hydroxy, halo and $C_{1-6}$alkyl; or a radical of formula (c-1), (c-3) or (c-4) wherein R$^{13}$ is $C_{1-4}$alkyl; or L is a radical of formula (b-2), wherein Alk is $C_{1-6}$alkanediyl, X is O, and R$^7$ is $C_{1-6}$alkyl or hydroxy$C_{1-6}$alkyl; or L is a radical of formula (b-2), wherein Alk is $C_{1-6}$alkanediyl, R$^7$ is Het$^2$ wherein Het$^2$ is pyrazinyl substituted with $C_{1-6}$alkyl, and X is NR$^8$ wherein R$^8$ is hydrogen or $C_{1-6}$alkyl; or L is a radical of formula (b-3) wherein Y is a direct bond, and R$^9$ is $C_{1-6}$alkyl, hydroxy or $C_{1-6}$alkyloxy; or L is a radical of formula (b-4) wherein Y is a direct bond, and R$^{11}$ and R$^{12}$ are $C_{1-6}$alkyl, or R$^{11}$ and R$^{12}$ combined with the nitrogen atom bearing R$^{11}$ and R$^{12}$ form pyrrolidinyl.

4. The compound as claimed in claim 1 wherein L is butyl; propyl substituted with methoxy, methylcarbonyl or 2-methyl-1,3-dioxolane; ethyl substituted with 4-methyl-2-pyridazinone or tetrahydropyranyl; or methyl substituted with tetrahydrofuranyl or tetrahydropyranyl.

5. A pharmaceutical composition comprising a pharmaceutically acceptable carrier and a therapeutically active amount of a compound according to claim 1.

6. A compound of formula (III)

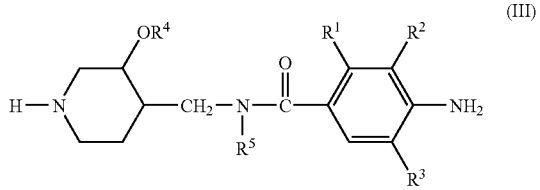
(III)

a pharmaceutically acceptable acid addition salt thereof or a stereochemically isomeric form thereof, wherein R$^1$, R$^2$, R$^3$, R$^4$ and R$^5$ are as defined in claim 1 for compounds of formula (I).

7. A process for preparing a compound of formula (I) wherein a) an intermediate of formula (II) is N-alkylated with an intermediate of formula (III) in a reaction-inert solvent and, optionally in the presence of a suitable base,

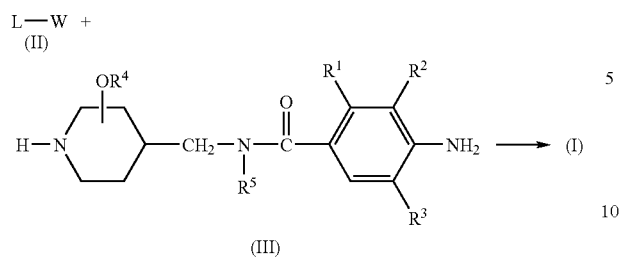

(II)

(III)

b) an appropriate ketone or aldehyde intermediate of formula L'=O(IV), said L'=O being a compound of formula L-H, wherein two geminal hydrogen atoms in the $C_{1-12}$alkanediyl moiety are replaced by =O, is reacted with an intermediate of formula (III);

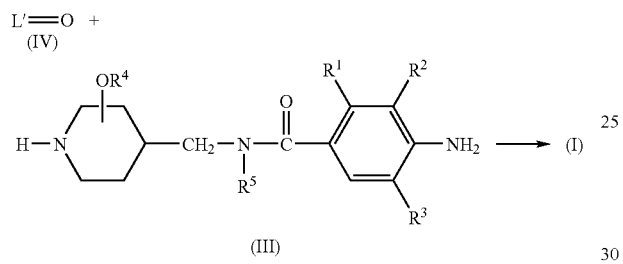

(IV)

(III)

c) an intermediate of formula (V) is reacted with an carboxylic acid derivative of formula (VI) or a reactive functional derivative thereof;

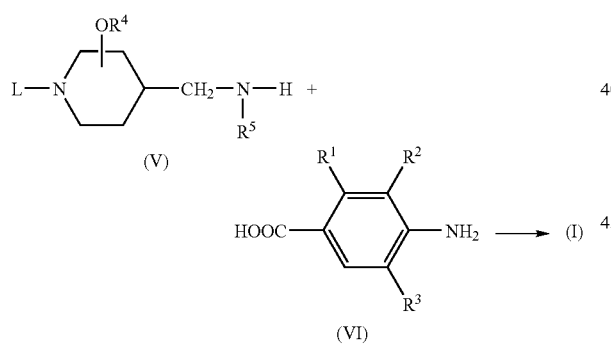

(V)

(VI)

d) an intermediate of formula (VII), wherein X is bromo or iodo, is carbonylated in the presence of an intermediate of formula (V) in a reaction-inert solvent in the presence of a suitable catalyst and a tertiary amine, and at a temperature ranging between room temperature and the reflux temperature of the reaction mixture;

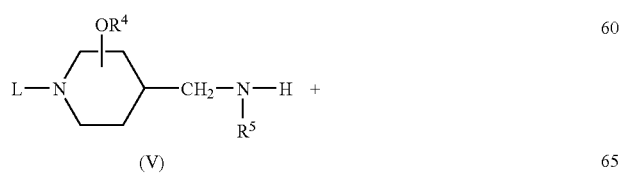

(V)

-continued

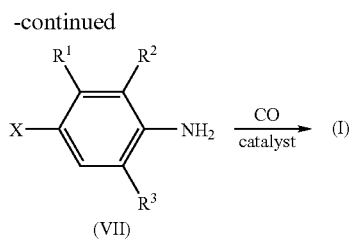

(VII)

wherein in the above reaction schemes the radicals L, $R^1$, $R^2$, $R^3$, $R^4$ and $R^5$ are as defined in claim 1 and wherein the —$OR^4$ radical is situated at the 3 position of the central piperidine moiety, and W is an appropriate leaving group;

e) or, compounds of formula (I) are converted into each other following art-known transformation reactions; or if desired; a compound of formula (I) is converted into a pharmaceutically acceptable acid addition salt, or conversely, an acid addition salt of a compound of formula (I) is converted into a free base form with alkali; and, if desired, preparing stereochemically isomeric forms thereof.

8. A process for preparing a compound of formula (III) wherein a) an intermediate of formula (VIII), wherein PG is an appropriate protective group, is reacted with an acid of formula (VI), or an appropriate reactive functional derivative thereof, in a reaction-inert solvent and subsequent deprotection of the protecting group PG yielding compounds of formula (III);

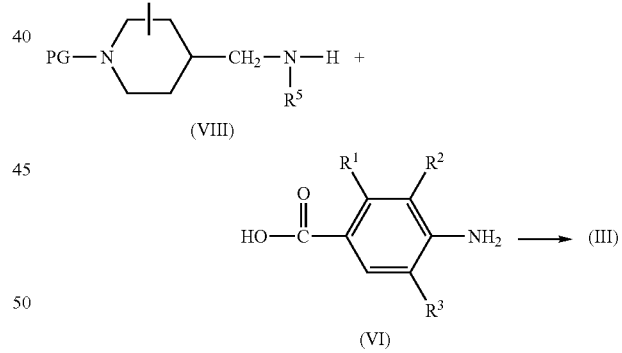

(VIII)

(VI)

wherein in the above reaction schemes the radicals L, $R^1$, $R^2$, $R^3$, $R^4$ and $R^5$ are as defined in claim 1 and wherein the —$OR^4$ radical is situated at the 3 position of the central piperidine moiety, and W is an appropriate leaving group;

b) or, compounds of formula (III) are converted into each other following art-known transformation reactions; or if desired; a compound of formula (III) is converted into an acid addition salt, or conversely, an acid addition salt of a compound of formula (III) is converted into a free base form with alkali; and, if desired, preparing stereochemically isomeric forms thereof.

9. A method of treating decreased gastro-intestinal motility comprising administering to a subject in need thereof an effective amount of a compound according to claim 1.

10. A process for preparing a pharmaceutical composition comprising mixing a therapeutically effective amount of a compound according to claim 1 with a pharmaceutically acceptable carrier.

* * * * *

UNITED STATES PATENT AND TRADEMARK OFFICE
CERTIFICATE OF CORRECTION

PATENT NO.       : 7,790,750 B2
APPLICATION NO.  : 11/584732
DATED            : September 7, 2010
INVENTOR(S)      : Jean-Paul René Marie André Bosmans et al.

It is certified that error appears in the above-identified patent and that said Letters Patent is hereby corrected as shown below:

Title Page,
Item (60) Related U.S. Application Data:
Line 7, after "now abandoned" insert -- which is a continuation of U.S. application No. 09/113,635 filed on July 10, 1998, now abandoned, which claims priority to EP application No. 98.200624.9 filed February 27, 1998 and EP application No. 97.202180.2 filed July 11, 1997. --.

Title Page,
Item (30) Foreign Application Priority Data:
After "97202180" insert -- .2 --.
After "98200624" insert -- .9 --.

Column 20,
Line 11, delete ""DEPE"" and insert -- "DIPE" --.

Column 39,
Line 32, delete "TABLE F-8" and insert -- TABLE F-5 --.

Column 40,
Line 1, delete "TABLE F-8-continued" and insert -- TABLE F-5-continued --.

Column 48,
Line 20, delete "tetrahydrofiaran;" and insert -- tetrahydrofuran; --.

Signed and Sealed this
Nineteenth Day of July, 2011

David J. Kappos
*Director of the United States Patent and Trademark Office*